United States Patent [19]
Harada et al.

[11] Patent Number: 5,854,407
[45] Date of Patent: *Dec. 29, 1998

[54] 15-HYDROXY 6,9-HEMIACETAL ERYTHROMYCIN COMPOUNDS

[75] Inventors: Setsuo Harada, Kawanishi; Yasunori Funabashi, Osaka; Nobuhiro Inatomi, Osaka; Shigeharu Tanayama, Osaka; Seiichi Tanida, Kyoto, all of Japan

[73] Assignee: Takeda Chemical Corporation, Osaka, Japan

[*] Notice: The term of this patent shall not extend beyond the expiration date of Pat. No. 5,470,961.

[21] Appl. No.: 475,557

[22] Filed: Jun. 7, 1995

Related U.S. Application Data

[62] Division of Ser. No. 33,777, Mar. 19, 1993, Pat. No. 5,470,961.

[30] Foreign Application Priority Data

Mar. 19, 1992 [JP] Japan .................................. 4-064243
Jun. 11, 1992 [JP] Japan .................................. 4-152467

[51] Int. Cl.$^6$ .................................................. C07H 17/08
[52] U.S. Cl. .............................. 536/7.2; 514/29; 536/7.3; 536/7.4
[58] Field of Search ............................. 536/7.2, 7.3, 7.4; 514/29, 892

[56] References Cited

U.S. PATENT DOCUMENTS 5,470,961  11/1995  Harada et al. ............................ 536/7.4

FOREIGN PATENT DOCUMENTS 0213617  3/1987  European Pat. Off. .
0215355  3/1987  European Pat. Off. .
022186   5/1987  European Pat. Off. .
0349100  1/1990  European Pat. Off. .

OTHER PUBLICATIONS

Tsuzuki, Kazuo, Chem. Pharm. Bull 37 (10) 2687–2700 (1989).

Omura, Satoshi, et al., Journal of Medicine Chem., vol. 30:11 1941–1943 (1987).

*Primary Examiner*—John Kight
*Assistant Examiner*—Howard C. Lee
*Attorney, Agent, or Firm*—David G. Conlin; Ronald I. Eisenstein; Dike, Bronstein, Roberts & Cushman, LLP

[57] ABSTRACT

Disclosed are (1) a structurally novel 6,9-hemiacetal- erythromycin derivative having a hydroxyl group at at least one of the 14- and 15-positions br a salt thereof, which has an excellent gastrointestinal function promoting effect and is low in toxicity; (2) a process for preparing a 6,9-hemiacetal-erythromycin derivative having a hydroxyl group at at least one of the 14- and 15-positions or a salt thereof, which comprises reacting a 6,9-hemiacetal-erythromycin derivative or a salt thereof with an organism-derived oxidase; and (3) a gastrointestinal function promoting agent containing a 6,9-hemiacetal-erythromycin derivative having a hydroxyl group at at least one of the 14- and 15-positions or a salt thereof.

23 Claims, 14 Drawing Sheets

FIG. I

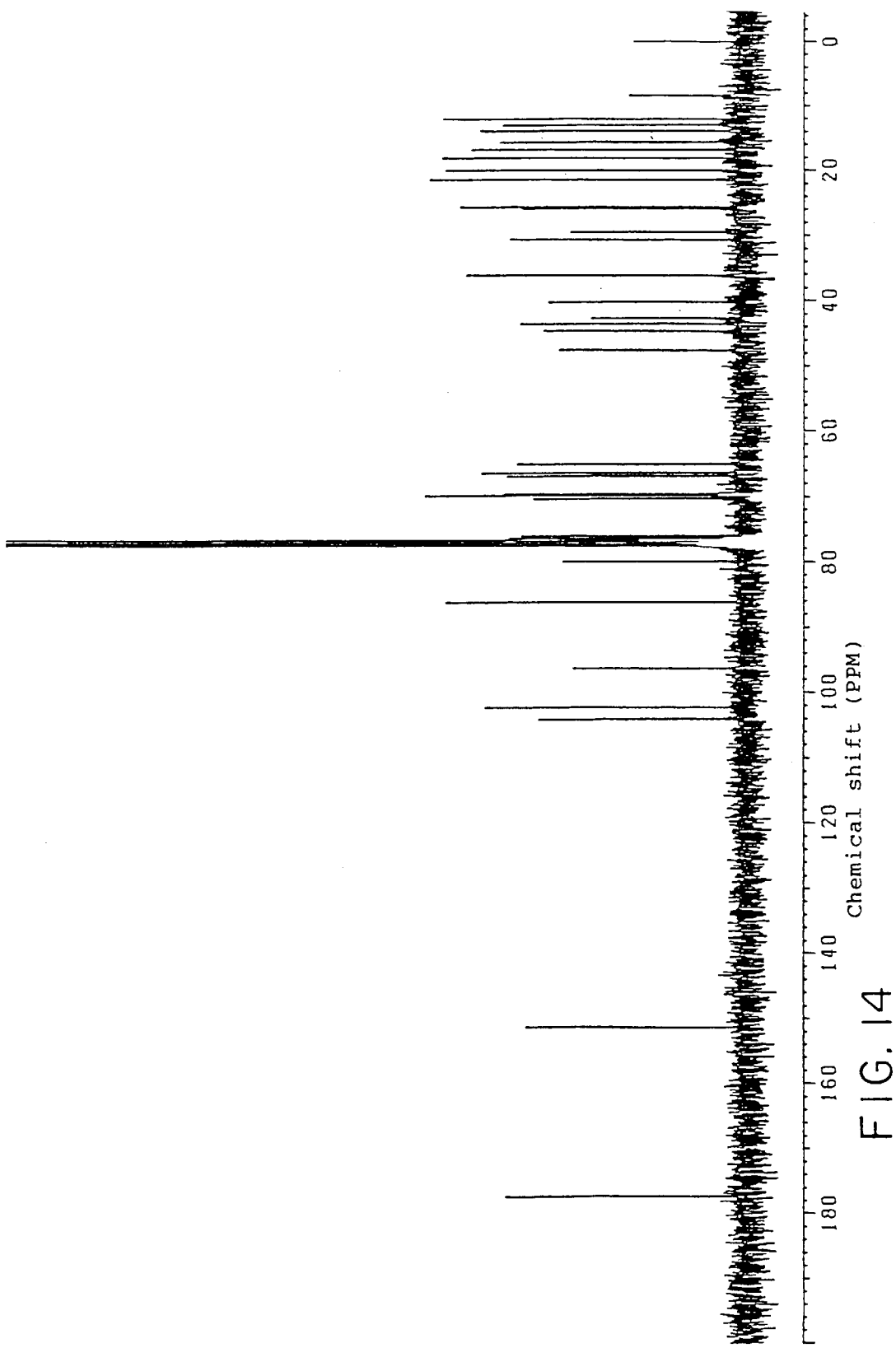

15-HYDROXY 6,9-HEMIACETAL ERYTHROMYCIN COMPOUNDS

This is a divisional of application(s) Ser. No. 08/033,777, filed on Mar. 19, 1993, now U.S. Pat. No. 5,470,961.

BACKGROUND OF THE INVENTION

The present invention relates to novel compounds useful as gastrointestinal function promoting agents. More particularly, the present invention relates to the application of novel derivatives of erythromycin to gastrointestinal function promoting agents.

The antibiotic erythromycin, which belongs to the class of basic 14-membered ring macrolides, is produced from microorganisms such as the strains described in J. M. McGuire et al., *Antibiotics & Chemotherapy*, 2, 281–283 (1952) and D. P. Labeda et al., *Int. J. Syst. Bacteriol.*, 37, 19–22 (1987) and represented by *Streptomyces erythreus* (*Saccharopolyspora erythraea*), and is composed of erythromycins A, B, C and D as shown below [P. F. Wiley et al., *J. Amer. Chem. Soc.*, 79, 6062–6070, 6070–6073, 6074–6077 (1957); J. Majer et al., *J. Amer. Chem. Soc.*, 99, 1620–1622 (1977)].

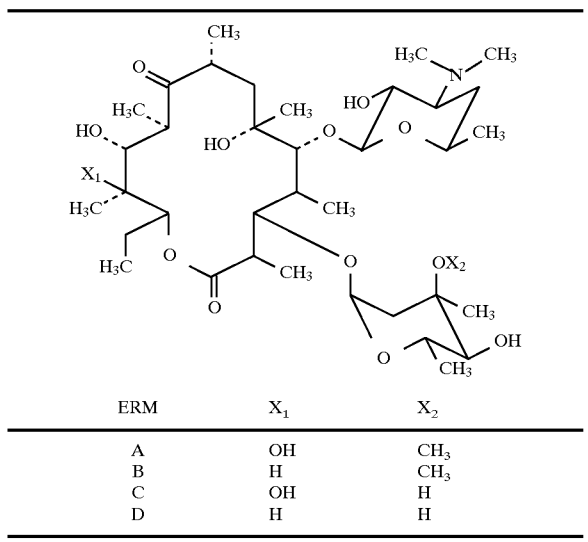

| ERM | $X_1$ | $X_2$ |
|-----|-------|-------|
| A   | OH    | $CH_3$ |
| B   | H     | $CH_3$ |
| C   | OH    | H     |
| D   | H     | H     |

Erythromycin (hereinafter sometimes abbreviated as ERM) A in its use as an antibacterial agent can have side effects such as vomiting. Z. Itoh et al. has reported that ERM A has motilin-like action promoting the gastrointestinal peristaltic movement [gastrointestinal motor stimulating (hereinafter occasionally reffered to as GMS) activity] [Am. J. Physiol., 247, G688–694 (1984)]. S. Omura et al. reported preparing ERM derivatives having a strong GMS activity in which little antibacterial effect was observed, and filed applications for patents (EP-A-213617 and EP-A-215355). Manufacturing methods, properties, structures and biological activity of these derivatives are described in *J. Med. Chem.*, 30, 1941–1943 (1987) and *Chem. Pharm. Bull.*, 37, 2687–2700, 2701–2709 (1989).

Humans eat food to support life and to maintain and restore physical strength. However, an individual's whose digestive function or whose gastrointestinal motor function is lowered, such as a patient after an operation, a patient with a grave infectious disease or cancer, a patient with diabetes in whom a gastrointestinal functional disorder is observed, a patient with chronic gastritis or a patient with regurgitant esophagitis, requires a drug to activate the gastrointestinal motor function. Accordingly, the development of an excellent gastrointestinal motor promoting agent is needed.

SUMMARY OF THE INVENTION

The present inventors have now discovered that an erythromycin derivative having a hydroxyl group at at least one of the 14- and 15-positions promoted the gastrointestinal motor function (had GMS activity), when given to the animals.

Namely, the present inventors found an active metabolite in vivo which promoted the gastrointestinal motor function (had GMS activity), when compound (1) or (2) of 14-membered ring macrolides having the structural formula shown in Table 1 below were given to the animals. Compound (1) was intravenously given to the dogs, followed by solvent extraction from the livers 30 minutes after administration, chromatography and preparative HPLC to obtain two active metabolites, compounds (3) and (4). The present inventors were able to determine that the chemical structures of these compounds were 15- and 14-hydroxyl derivatives of compound (1), respectively. Compound (2) was treated similarly to obtain corresponding compounds (7) and (8). All of these compounds are novel compounds and we were able to demonstrate that they had a strong gastrointestinal motor promoting effect in in vivo test of dogs.

As a result of further investigations, the present inventors discovered that erythromycin derivatives having a hydroxyl group at at least one of the 14- and 15- positions promoted gastrointestinal motor function, and that its activity was equivalent or higher than that of derivatives having no hydroxyl group at both 14- and 15- positions.

These compounds can be formed by an oxidation reaction.

In the above-mentioned oxidation reaction, animal-derived oxidases can be used. For preparing the samples in large amounts, the present inventors determined microorganisms which produce enzymes for allowing such oxidation reaction to proceed. As a result, the present inventors discovered that certain kinds of microorganisms had this ability.

Based on these findings, the present inventors have resulted in the present invention.

Namely, the present invention provides:

(1) a structurally novel 6,9-hemiacetal-erythromycin derivative having a hydroxyl group at at least one of the 14- and 15-positions or a salt thereof;

(2) a process for preparing a 6,9-hemiacetal-erythromycin derivative having a hydroxyl group at at least one of the 14- and 15-positions or a salt thereof, which comprises allowing a 6,9-hemiacetal-erythromycin derivative or a salt thereof to react with an organism-derived oxidase; and (3) a gastrointestinal function promoting agent containing a 6,9-hemiacetal-erythromycin derivative having a hydroxyl group at at least one of the 14- and 15-positions or a salt thereof.

BRIEF DESCRIPTION OF THE DRAWINGS

FIG. 14 shows a $^{13}C$ NMR spectrum of the compound (9);

DESCRIPTION OF THE PREFERRED EMBODIMENTS

Figure 1:
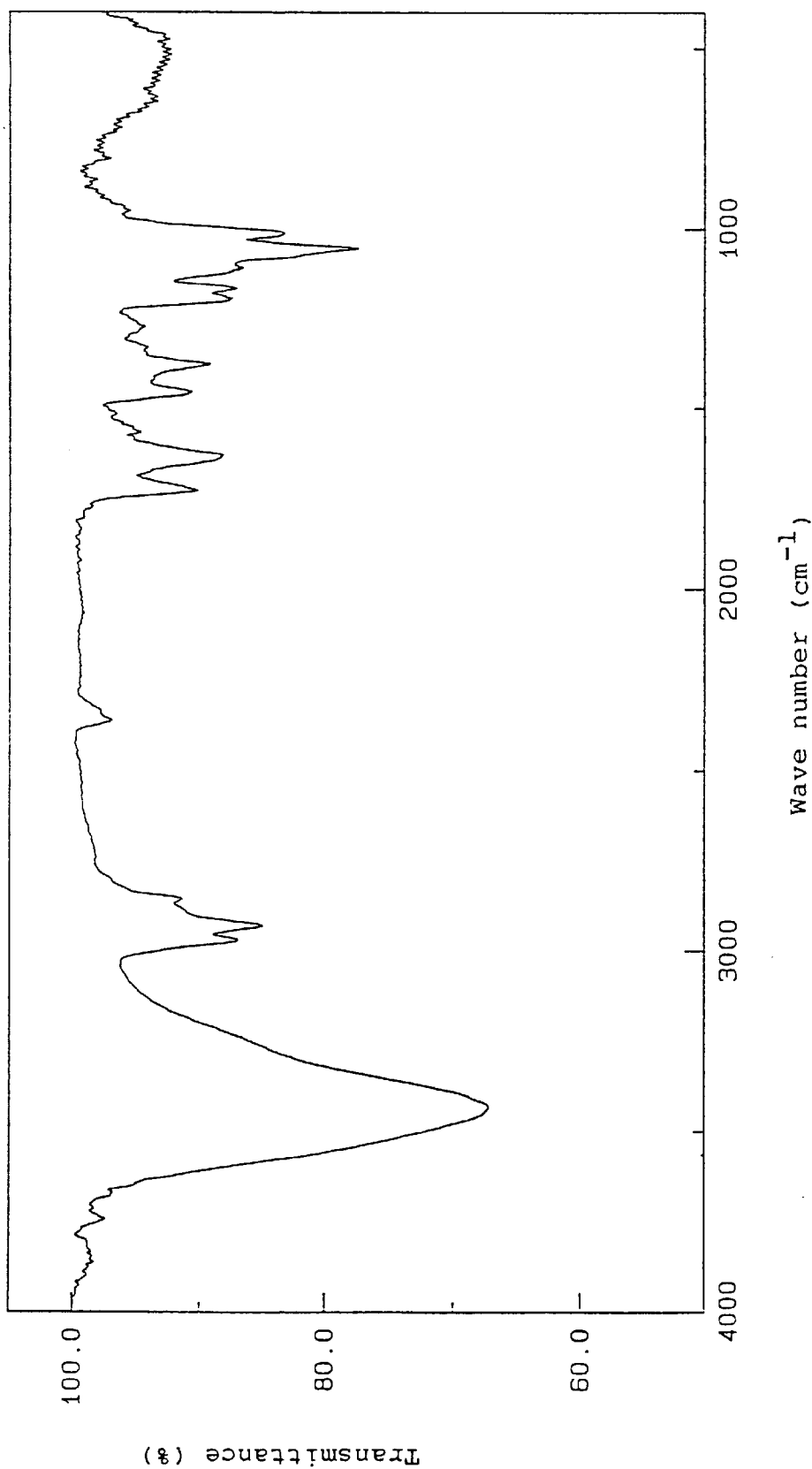
FIG. 1 shows an IR spectrum of a compound (7)

The 6,9-hemiacetal-erythromycin derivatives of the present invention include a 6,9-hemiacetal-erythromycin derivative represented by the general formula [1]:

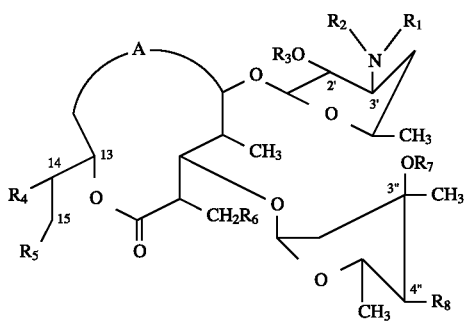

wherein $R_1$ represents hydrogen or a substituted or unsubstituted aliphatic hydrocarbon group and $R_2$ represents hydrogen or a substituted or unsubstituted aliphatic hydrocarbon group, or $R_1$ and $R_2$ can form a heterocyclic group together with the adjacent nitrogen atom; $R_3$ represents hydrogen or a substituted or unsubstituted acyl group; $R_4$ and $R_5$ represent hydrogen or hydroxyl groups, at least one of $R_4$ and $R_5$ is a hydroxyl group; $R_6$ represents hydrogen or a hydroxyl group; $R_7$ represents hydrogen or a methyl group; $R_8$ represents hydrogen, a hydroxyl group, a substituted or unsubstituted acyloxy group or a substituted or unsubstituted alkoxy group;

and —A— represents the following general formula [2]:

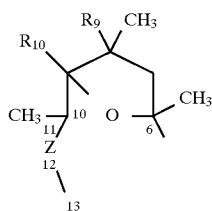

wherein $R_9$ and $R_{10}$ both represent hydrogen or both form a chemical bond; and Z represents the general formula [3]:

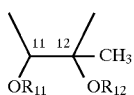

wherein $R_{11}$ represents hydrogen, a substituted or unsubstituted acyl group or a substituted or unsubstituted alkyl group; and $R_{12}$ represents hydrogen, a lower carboxylacyl group or an alkyl group which may have alkylthio as a substituent, or Z represents the general formula [4]:

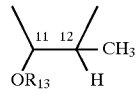

wherein $R_{13}$ represents hydrogen, a substituted or unsubstituted acyl group or a substituted or unsubstituted alkyl group, or Z represents the formula [5]:

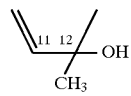

or Z represents the formula [6]:

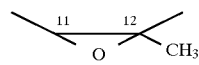

or Z represents the general formula [7]:

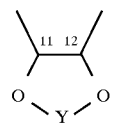

wherein Y represents the formula >B—$R_{14}$ ;wherein $R_{14}$ represents an alkyl group or an aryl group: >S=O, >C=O, >C=S or the general formula [8]:

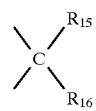

wherein $R_{15}$ and $R_{16}$, which may be the same or different, represent hydrogen or alkyl groups, or form a cyclic alkyl group together with the adjacent carbon atom, or one of $R_{15}$ and $R_{16}$ represents hydrogen, an alkyl group or an aryl group, and the other represents a dialkylamino group, or —A— represents the general formula [9]:

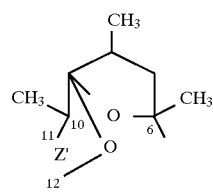

wherein Z' represents the general formula [10]:

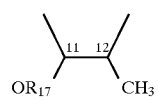

wherein $R_{17}$ represents hydrogen, a substituted or unsubstituted acyl group or a substituted or unsubstituted alkyl group.

The above-mentioned 6,9-hemiacetal-erythromycin derivatives include a 6,9-hemiacetal-erythromycin derivative represented by the general formula [11]:

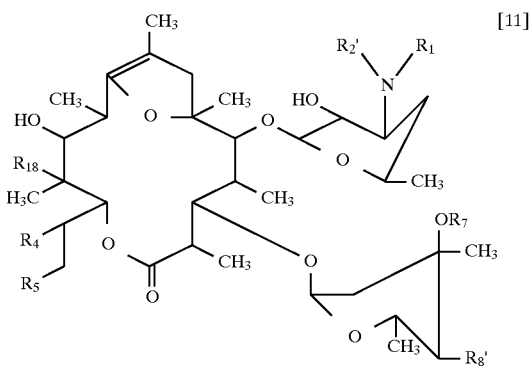

[11]

wherein $R_1$ represents hydrogen or a substituted or unsubstituted aliphatic hydrocarbon group; $R_2'$ represents a substituted or unsubstituted aliphatic hydrocarbon group; $R_4$ and $R_5$ represent hydrogen or hydroxyl groups, at least one of $R_4$ and $R_5$ is a hydroxyl group; $R_7$ represents hydrogen or a methyl group; $R_8'$ represents hydrogen or a hydroxyl group; and $R_{18}$ represents hydrogen or a hydroxyl group.

The above-mentioned 6,9-hemiacetal-erythromycin derivative include a 6,9-hemiacetal-erythromycin derivative represented by the general formula [12]:

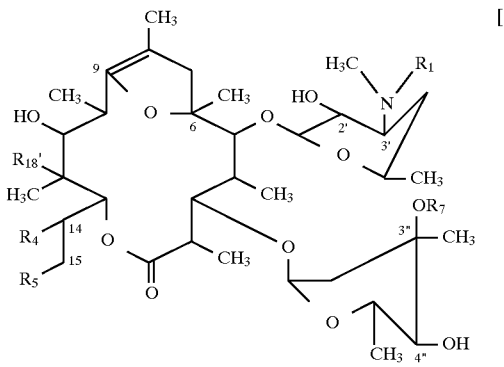

[12]

wherein $R_1$ represents hydrogen or a substituted or unsubstituted aliphatic hydrocarbon group, $R_{18}'$ represents hydrogen or a hydroxyl group, $R_4$ and $R_5$ represent hydrogen or hydroxyl groups, at least one of $R_4$ and $R_5$ is a hydroxyl group, $R_7$ represents hydrogen or methyl group, with proviso that $R_{18}'$ represents hydrogen when $R_7$ is methyl.

The above-mentioned 6,9-hemiacetal-erythromycin derivatives include a 6,9-hemiacetal-erythromycin derivative represented by the general formula [13]:

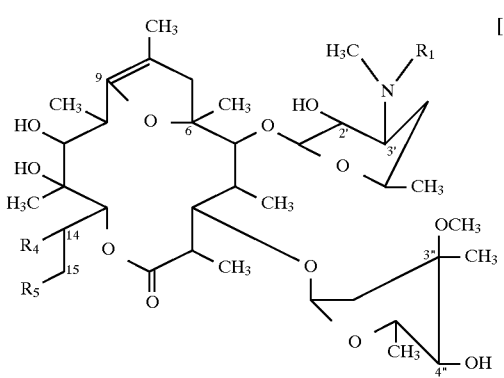

[13]

wherein $R_1$ represents hydrogen or a substituted or unsubstituted aliphatic hydrocarbon group, $R_4$ and $R_5$ represent hydrogen or hydroxyl groups, at least one of $R_4$ and $R_5$ is a hydroxyl group.

The preferred 6,9-hemiacetal-erythromycin derivatives represented by the formula [11] include those in which $R_1$ and $R_2$ may be same or different and represent a substituted or unsubstituted lower alkyl group or a substituted or unsubstituted cycloalkyl group.

The more preferred 6,9-hemiacetal-erythromycin derivatives represented by the formula [11] include those in which $R_1$ and $R_2$ may be same or different and represent a substituted or unsubstituted $C_{1-6}$ alkyl group.

The preferred 6,9-hemiacetal-erythromycin derivatives represented by the formula [12] or [13] include those in which $R_1$ is isopropyl or ethyl group.

The 6,9-hemiacetal-erythromycin derivatives of the present invention can be prepared by an oxidation reaction using an organism-derived oxidase as described below.

The process of the present invention for preparing the 6,9-hemiacetal-erythromycin derivative represented by the formula [1] or the salt thereof comprises reacting a 6,9-hemiacetal-erythromycin derivative represented by the general formula [14]:

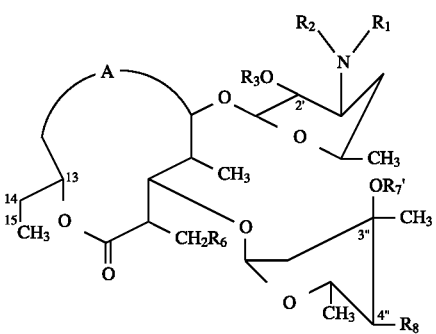

[14]

wherein $R_7'$ represents hydrogen or a methyl group, and other symbols have the same meanings as defined above, or a salt thereof with an organism-derived oxidase.

The above-mentioned process for preparing the 6,9-hemiacetal-erythromycin derivative represented by the formula [11] or the salt thereof comprises allowing a 6,9-hemiacetal-erythromycin derivative represented by the general formula [15] or a salt thereof to react with an organism-derived oxidase:

[15]

wherein $R_1$, $R_2'$, $R_7'$, $R_8'$ and $R_{18}$ have the same meanings as defined above.

The above-mentioned process for preparing the 6,9-hemiacetal-erythromycin derivative represented by the general formula [16]:

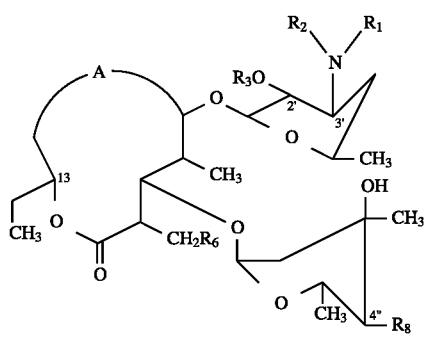

wherein $R_1$ represents hydrogen or a substituted or unsubstituted aliphatic hydrocarbon group and $R_2$ represents hydrogen or a substituted or unsubstituted aliphatic hydrocarbon group, or $R_1$ and $R_2$ form a heterocyclic group together with the adjacent nitrogen atom; $R_3$ represents hydrogen or a substituted or unsubstituted acyl group; $R_6$ represents hydrogen or a hydroxyl group; $R_8$ represents hydrogen, a hydroxyl group, a substituted or unsubstituted acyloxy group or a substituted or unsubstituted alkoxy group, and —A— represents the general formula [2]:

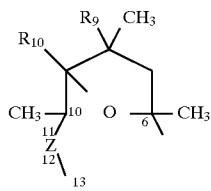

wherein $R_9$ and $R_{10}$ both represent hydrogen or both form a chemical bond;
and Z represents the general formula [3]:

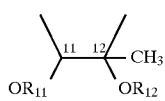

wherein $R_{11}$ represents hydrogen, a substituted or unsubstituted acyl group or a substituted or unsubstituted alkyl group; and $R_{12}$ represents hydrogen, a lower carboxylacyl group or an alkyl group which may have alkylthio as a substituent, or Z represents the general formula [4]:

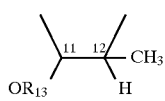

wherein $R_{13}$ represents hydrogen, a substituted or unsubstituted acyl group or a substituted or unsubstituted alkyl group, or Z represents the formula [5]:

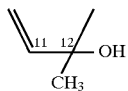

or Z represents the formula [6]:

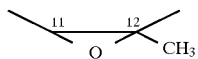

or Z represents the general formula [7]:

wherein Y represents the formula $>B$—$R_{14}$; wherein $R_{14}$ represents an alkyl group or an aryl group; $>S=O$, $>C=O$, $>C=S$ or the general formula [8]:

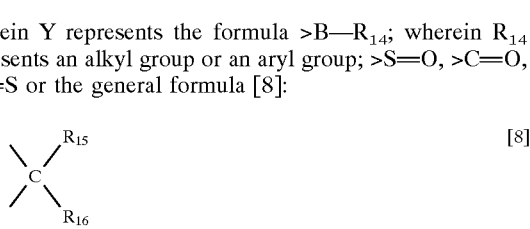

wherein $R_{15}$ and $R_{16}$, which may be the same or different, represent hydrogen or alkyl groups or form a cyclic alkyl group together with the adjacent carbon atom, or one of them represents hydrogen, an alkyl group or an aryl group, and the other represents a dialkylamino group, or -A- represents the general formula [9]:

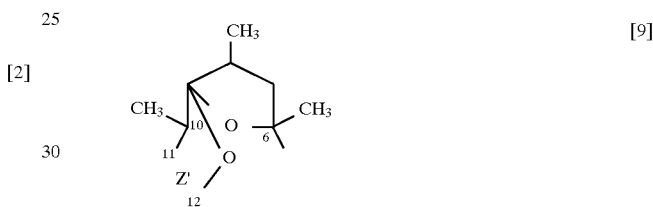

wherein Z' represents the general formula [10]:

wherein $R_{17}$ represents hydrogen, a substituted or unsubstituted acyl group or a substituted or unsubstituted alkyl group, or the salt thereof, comprises reacting a 6,9-hemiacetal-erythromycin derivative represented by the general formula [17]

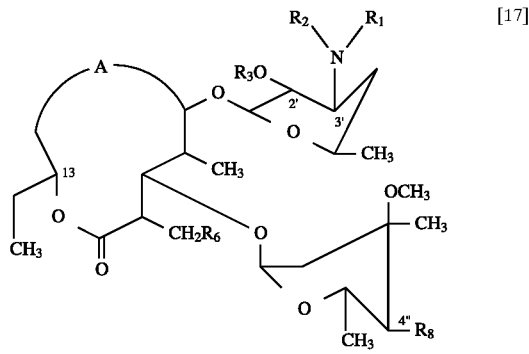

wherein $R_1$, $R_2$, $R_3$, $R_6$, $R_8$ and —A— have the same meanings as defined above, or a salt thereof with the organism-derived oxidase.

The above-mentioned process for preparing the 6,9-hemiacetal-erythromycin derivative represented by the general formula [18]:

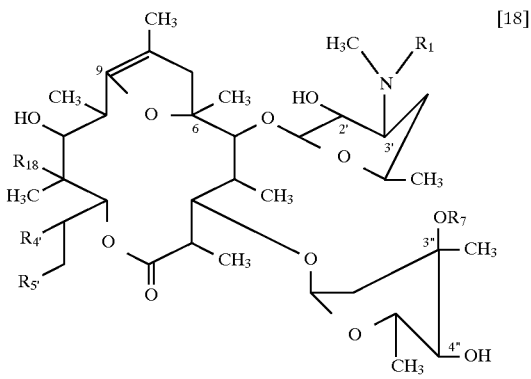

[18]

wherein $R_1$ represents hydrogen or a substituted or unsubstituted aliphatic hydrocarbon group, $R_{18}$ represents hydrogen or a hydroxyl group, $R_4'$ and $R_5'$ represent hydrogen or hydroxyl groups, $R_7$ represents hydrogen or methyl group, with proviso that $R_7$ represents hydrogen when both of $R_4'$ and $R_5'$ are hydrogens, or the salt thereof, in which a 6,9-hemiacetal-erythromycin derivative represented by the general formula [19]:

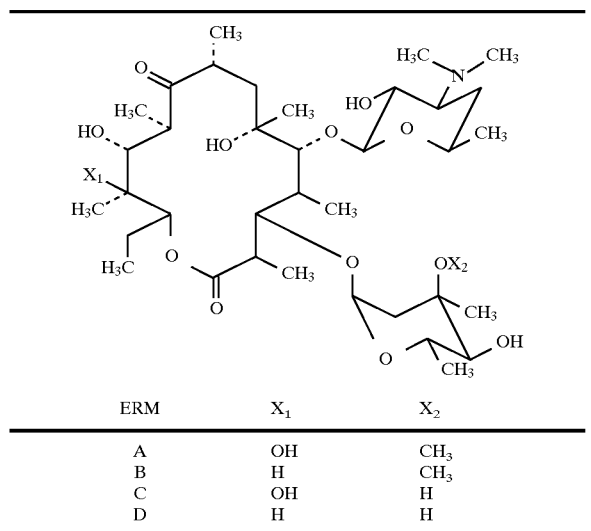

| ERM | $X_1$ | $X_2$ |
|---|---|---|
| A | OH | $CH_3$ |
| B | H | $CH_3$ |
| C | OH | H |
| D | H | H | wherein $R_1$, $R_{18}$, and $R_7'$, have the same meaning as defined above or a salt thereof, comprises allowing the compound represented by formula [19] to react with the organism-derived oxidase.

The compound represented by the formula [14], [15] or [19] wherein $R_7'$ is a methyl group may be converted by the oxidation reaction to the compound wherein $R_7$ is a hydrogen.

In the formulae represented by the above formulae preferably ([1], [11], [12], [13], [14], [15], [16], [17], [18] and [19] described in the claims shown below and standing for the examples of the desired derivatives of the present invention and the examples of the starting materials used in the present invention, the aliphatic hydrocarbon groups of the substituted or unsubstituted aliphatic hydrocarbon groups, represented by $R_1$, include, for example, lower alkyl, cycloalkyl, lower alkenyl and lower alkynyl. These groups should preferably include not more than 12 carbon atoms, more preferably, not more than about 6 carbon atoms. Lower alkyl and cycloalkyl are preferred and lower alkyl is more preferred. When substituted, these groups may have 1 to 3 appropriate substituents.

As the lower alkyl groups, alkyl groups of 1 to 6 carbon atoms are more preferred. Examples thereof include methyl, ethyl, propyl, isopropyl, butyl, isobutyl, pentyl and hexyl. The lower alkyl groups are still more preferably alkyl groups of 1 to 3 carbon atoms, and even more preferably methyl, ethyl and isopropyl.

Examples of the cycloalkyl groups preferably include cycloalkyl groups of 3 to 7 carbon atoms such as cyclopropyl, cyclobutyl, cyclopentyl, cyclohexyl and cycloheptyl. The cycloalkyl groups are more preferably cycloalkyl groups of 4 to 6 carbon atoms such as cyclobutyl, cyclopentyl and cyclohexyl.

Preferred examples of the lower alkenyl groups include alkenyl groups of 2 to 6 carbon atoms such as vinyl, allyl, 2-butenyl, methylallyl, 3-butenyl, 2-pentenyl, 4-pentenyl and 5-hexenyl.

Preferred examples of the lower alkynyl groups include alkynyl groups of 2 to 6 carbon atoms such as ethynyl, propargyl, 2-butyn-1-yl, 3-butyn-2-yl, 1-pentyn-3-yl, 3-pentyn-1-yl, 4-pentyn-2-yl and 3-hexyn-1-yl.

The substituents on the substituted or unsubstituted aliphatic hydrocarbon groups include, for example, hydroxyl, azido, nitro, amino, cyano, guanidino, amidino, sulfo, carboxy, oxo, epoxy, thioxo, sulfoamino, sulfamoyl, sulfamoylamino, ureido, benzoyl, halogen, $C_{3-6}$ cycloalkyl, $C_{6-10}$ aryl, $C_{1-4}$ alkoxy, $C_{1-4}$ alkoxy-$C_{2-3}$ alkyl, $C_{3-6}$ cycloalkyloxy, $C_{6-10}$ aryloxy, $C_{7-12}$ aralkyloxy, $C_{1-4}$ alkylthio, $C_{3-6}$ cycloalkylthio, $C_{6-10}$ arylthio, $C_{7-12}$ aralkylthio, mono $C_{1-4}$ alkylamino, di $C_{1-4}$ alkylamino, $C_{3-6}$ cycloalkylamino, $C_{6-10}$ arylamino, $C_{7-12}$ aralkylamino, $C_{1-4}$ alkoxycarbonyl, $C_{6-10}$ aryloxycarbonyl, $C_{3-6}$ cycloalkyloxycarbonyl, $C_{7-12}$ aralkyloxycarbonyl, $C_{1-5}$ alkanoyl, $C_{1-15}$ alkanoyloxy, carbamoyl which may be substituted, carbamoyloxy which may be substituted, $C_{1-4}$ alkoxycarbonyloxy, $C_{7-12}$ aralkyloxycarbonyloxy, $C_{1-4}$ alkanoylamino, $C_{6-10}$ arylcarbonylamino, $C_{1-4}$ alkoxycarbonylamino, $C_{7-12}$ aralkyloxycarbonylamino, $C_{1-4}$ alkylsulfonylamino, $C_{6-10}$ arylsulfonylamino, $C_{1-4}$ alkylsulfinyl, $C_{6-10}$ arylsulfinyl, $C_{1-4}$ alkylsulfonyl, $C_{6-10}$ arylsulfonyl, $C_{1-4}$ alkylsulfonyloxy, $C_{6-10}$ arylsulfonyloxy, heterocyclic groups, heterocyclic thio, heterocyclic carbonylamino, heterocyclic oxy and heterocyclic amino.

The substituents on the above-mentioned aliphatic hydrocarbon groups, (1) $C_{3-6}$ cycloalkyl group, (2) $C_{6-10}$ aryl group, (3) alkyl groups in $C_{1-4}$ alkylthio, $C_{1-4}$ alkylsulfinyl, $C_{1-4}$ alkylsulfonyl and $C_{1-4}$ alkylsulfonyloxy, and (4) heterocyclic groups in the heterocyclic groups, heterocyclic thio, heterocyclic carbonylamino, heterocyclic oxy and heterocyclic amino, may further have appropriate substituents such as hydroxyl, azido, nitro, amino, cyano, sulfo, carboxy, oxo, halogen, $C_{1-4}$ alkyl, $C_{1-4}$ alkoxy, $C_{1-4}$ alkylthio, $C_{1-4}$ alkylamino, di $C_{1-4}$ alkylamino, $C_{5-10}$ arylamino, $C_{1-4}$ alkoxycarbonyl, $C_{6-10}$ aryloxycarbonyl, $C_{1-5}$ alkanoyl, $C_{1-5}$ alkanoyloxy, carbamoyl, carbamoyloxy, $C_{1-4}$ alkanoylamino, $C_{1-4}$ alkoxycarbonylamino and $C_{1-4}$ alkylsulfonylamino.

The number of the substituents on the above-mentioned respective groups is preferably 1 to 3.

These substituents will be described in detail below.

Examples of the halogen atoms include fluorine, chlorine, bromine and iodine.

Examples of the $C_{3-6}$ cycloalkyl groups include cyclopropyl, cyclobutyl, cyclopentyl and cyclohexyl.

Examples of the $C_{6-10}$ aryl groups include phenyl and naphthyl.

Examples of the $C_{1-4}$ alkoxy groups include methoxy, ethoxy, propoxy, isopropoxy, butoxy and tert-butoxy.

Examples of the $C_{1-4}$ alkoxy-$C_{2-3}$ alkyl groups include ethoxyethyl, methoxymethyl, dimethoxyethyl and diethoxyethyl.

Examples of the $C_{3-6}$ cycloalkyloxy groups include cyclopropyloxy, cyclobutyloxy, cyclopentyloxy and cyclohexyloxy.

Examples of the $C_{6-10}$ aryloxy groups include phenoxy and naphthyloxy.

Examples of the $C_{7-12}$ aralkyloxy groups include benzyloxy, 2-phenethyloxy and 1-phenethyloxy.

Examples of the $C_{1-4}$ alkylthio groups include methylthio, ethylthio, propylthio, isopropylthio, butylthio, isobutylthio, sec-butylthio and tert-butylthio.

Examples of the $C_{3-6}$ cycloalkylthio groups include cyclopropylthio, cyclopentylthio and cyclohexylthio.

Examples of the $C_{6-10}$ arylthio groups include phenylthio and naphthylthio.

Examples of the $C_{7-12}$ aralkylthio groups include benzylthio, 2-phenethylthio and 1-phenethylthio.

Examples of the mono $C_{1-4}$ alkylamino groups include methylamino, ethylamino, propylamino, isopropylamino, butylamino, isobutylamino and tert-butylamino.

Examples of the di $C_{1-4}$ alkylamino groups include dimethylamino, diethylamino, dipropylamino, dibutylamino, N-methyl-N-ethylamino, N-methyl-N-propylamino and N-methyl-N-butylamino.

Examples of the $C_{3-6}$ cycloalkylamino groups include cyclopropylamino, cyclobutylamino, cyclopentylamino and cyclohexylamino.

Examples of the $C_{6-10}$ arylamino groups include anilino and naphthylamino.

Examples of the $C_{7-12}$ aralkylamino groups include benzylamino, phenethylamino and phenylpropylamino.

Examples of the $C_{1-4}$ alkoxycarbonyl groups include methoxycarbonyl, ethoxycarbonyl, propoxycarbonyl, isopropoxycarbonyl, butoxycarbonyl, tert-butoxycarbonyl and isobutoxycarbonyl.

Examples of the $C_{6-10}$ aryloxycarbonyl groups include phenoxycarbonyl.

Examples of the $C_{3-6}$ cycloalkyloxycarbonyl groups include cyclopropyloxycarbonyl, cyclobutyloxycarbonyl, cyclopentyloxycarbonyl and cyclohexyloxycarbonyl.

Examples of the $C_{7-12}$ aralkyloxycarbonyl groups include benzyloxycarbonyl, 1-phenethyloxycarbonyl and 2-phenethyl-oxycarbonyl and phenylpropyloxycarbonyl.

Examples of the $C_{1-5}$ alkanoyl groups include formyl, acetyl, propionyl, butyryl and pivaloyl.

Examples of the $C_{1-15}$ alkanoyloxy groups include formyloxy, acetoxy, butyryloxy, pivaloyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy and pentadecanoyloxy.

Examples of the substituted carbamoyl groups include N-methylcarbamoyl, N,N-dimethylcarbamoyl, N-ethylcarbamoyl, N,N-diethylcarbamoyl, N-phenylcarbamoyl, pyrrolidino-carbamoyl, piperidinocarbamoyl, piperazinocarbamoyl, morpholinocarbamoyl and N-benzylcarbamoyl.

Examples of the substituted carbamoyloxy groups include N-methylcarbamoyloxy, N,N-dimethylcarbamoyloxy, N-ethylcarbamoyloxy, N-benzylcarbamoyloxy, N,N-dibenzyl-carbamoyloxy and N-phenylcarbamoyloxy.

Examples of the $C_{1-4}$ alkoxycarbonyloxy groups include ethoxycarbonyloxy, ethoxycarbonyloxy and tert-butoxycarbonyloxy.

Examples of the $C_{7-12}$ aralkyloxycarbonyloxy groups include a benzyloxycarbonyloxy, and the like.

Examples of the $C_{1-4}$ alkanoylamino groups include formylamino, acetylamino, propionylamino and butyrylamino.

Examples of the $C_{6-10}$ arylcarbonylamino groups include benzamino.

Examples of the $C_{1-4}$ alkoxycarbonylamino groups include methoxycarbonylamino, ethoxycarbonylamino, butoxy-carbonylamino and tert-butoxycarbonylamino.

Examples of the $C_{7-12}$ aralkyloxycarbonylamino groups include benzyloxycarbonylamino, 2-phenethyloxycarbonylamino and 1-phenethyloxycarbonylamino.

Examples of the $C_{1-4}$ alkylsulfonylamino groups include methanesulfonylamino, ethanesulfonylamino and butanesulfonylamino.

Examples of the $C_{6-10}$ arylsulfonylamino groups include benzenesulfonylamino and naphthalenesulfonylamino.

Examples of the $C_{1-4}$ alkylsulfinyl groups include methylsulfinyl, ethylsulfinyl, propylsulfinyl, butyl-sulfinyl, isobutylsulfinyl, sec-butylsulfinyl and tert-butylsulfinyl.

Examples of the $C_{6-10}$ arylsulfinyl groups include phenylsulfinyl and naphthylsulfinyl.

Examples of the $C_{1-4}$ alkylsulfonyl groups include methanesulfonyl, ethanesulfonyl and butanesulfonyl.

Examples of the $C_{6-10}$ arylsulfonyl groups include benzenesulfonyl, toluenesulfonyl and naphthalenesulfonyl.

Examples of the $C_{1-4}$ alkylsulfonyloxy groups include methanesulfonyloxy, ethanesulfonyloxy and butanesulfonyloxy.

Examples of the $C_{6-10}$ arylsulfonyloxy groups include benzenesulfonyloxy and toluenesulfonyloxy.

The heterocyclic groups include 5 or 6- membered cyclic groups containing 1 to 5 atoms of hetero atoms such as nitrogen, oxygen and sulfur. Examples thereof include pyrrolidinyl, pyrrolyl, pyrazolyl, imidazolyl, furyl, thienyl, oxazolyl, isooxazolyl, isothiazolyl, thiazolyl, piperidinyl, pyridyl, pyridazinyl, pyrazinyl, piperadinyl, pyrimidinyl, pyranyl, tetrahydropyranyl, tetrahydrofuryl, indolyl, quionlyl, 1,3,4-oxadiazolyl, 1,2,3-thiadiazolyl, 1,3,4-thiadiazolyl, 1,2,3-triazolyl, 1,2,4-triazolyl, 1,3,4-triazolyl, tetrazolyl, 1,3-dioxoranyl, morpholino and morpholinyl. The heterocyclic group may be condensed with a 5- or 6- membered ring which can contain 1 to 3 hetero atom(s) such as nitrogen and sulfur other than carbon atoms to form a condensed bicyclic group such as 8-quinolyl, 8-purinyl, thieno[2,3-d]pyridyl, tetrazolo[1,3-b]pyridazinyl, benzothiazolyl, benzooxazolyl, benzoimidazolyl and benzothienyl.

The heterocyclic thio, heterocyclic oxy, heterocyclic amino and heterocyclic carbonylamino groups include groups in which the above-mentioned heterocyclic rings are each bonded to sulfur atoms, oxygen atoms, nitrogen atoms or carbonylamino groups.

Preferred examples of substituents in the substituted lower alkyl, substituted cycloalkyl, substituted lower alkenyl and substituted lower alkynyl groups represented by $R_1$ include hydroxy, amino, sulpho, carboxy, halogen (such as chlorine, bromine, iodine and fluorine), aryl of 3 to 6 carbon atoms (such as phenyl, tolyl and naphthyl), lower alkoxy of 1 to 4 carbon atoms (such as methoxy, ethoxy, propoxy, isopropoxy and butoxy), lower alkylthio of 1 to 4 carbon atoms (methylthio, ethylthio, propylthio and butylthio), alkoxycarbonyloxy of 2 to 6 carbon atoms (such as tert-butoxycarbonyloxy), aralkyloxycarbonyloxy (such as benzyloxycarbonyloxy), substituted amino (such as dimethylamino and diethylamino), heterocyclic (cyclic amino) groups (such as morpholino, piperidino, pyrrolidinyl and 2-oxopyrrolidinyl), alkanoyloxy of 1 to 3 carbon atoms (such as formyloxy, acetoxy and trifluoroacetoxy), alkanoylamino of 1 to 4 carbon atoms (such as acetamido (acetylamino) and trifluoro-acetamido), lower alkoxy(of 1 to 4 carbon atoms)carbonyl (such as methoxycarbonyl, ethoxycarbonyl and butoxycarbonyl), carbamoyl and substituted carbamoyl (such as dimethylcarbamoyl and diethylcarbamoyl). Of these, halogen (such as chlorine, bromine, iodine and fluorine), hydroxyl and amino are preferred.

Concrete examples of the groups represented by $R_1$ include methyl, ethyl, isopropyl, chloromethyl, bromomethyl, iodomethyl, trifluoromethyl, chloroethyl, bromoethyl, iodoethyl, chloropropyl, hydroxymethyl, hydroxyethyl, hydroxypropyl, 2-hydroxy-2-phenylethyl, cyclopropylmethyl, cyclobutyl-methyl, cyclopentylmethyl, cyclohexylmethyl, 2-cyclohexyl-ethyl, 3-chlorocyclobutylmethyl, benzyl, 4-chlorobenzyl, 4-nitrobenzyl, 4-methoxybenzyl, 2,4-dimethoxybenzyl, 3,4-dimethoxybenzyl, 4-methylbenzyl, 2-ethoxyethyl, 2-(2,2,2-trifluoroethoxy)ethyl, methoxymethyl, 2,2-dimethoxyethyl, 2,2-diethoxyethyl, cyclopropylmethoxymethyl, cyclobutyl-methoxymethyl, 2-cyclopropylmethoxyethyl, 2-cyclobutyl-methoxyethyl, 2-benzyloxyethyl, 3-benzyloxypropyl, 2-phenoxyethyl, 3-phenylpropyl, methylthiomethyl, 2-methylthioethyl, 2-phenylthioethyl, 2-benzylthioethyl, 2-butylthioethyl, cyclohexylthiomethyl, 2-(4-pyridylthio)-ethyl, aminomethyl, aminoethyl, 2-methylaminoethyl, 2-tert-butylaminoethyl, 2-dimethylaminoethyl, 3-dimethylamino-propyl, 2-cyclohexylaminoethyl, 2-benzylaminoethyl, 2-azidoethyl, nitromethyl, 2-nitroethyl, cyanomethyl, 2-cyanoethyl, 4-cyanobutyl, carboxymethyl, 2-carboxyethyl, ethoxycarbonylmethyl, phenoxycarbonylmethyl, cyclopentyl-oxycarbonylmethyl, acetylmethyl, benzoylmethyl, 4-chlorobenzoylmethyl, 3-(4-bromobenzoyl)propyl, 3-methoxybenzoylmethyl, 2-formyloxyethyl, 2-methylsulfinyl-ethyl, 2-phenylsulfinylethyl, 2-methylsulfonylethyl, 3-phenylsulfonylpropyl, 2-acetoxyethyl, 4-acetoxybutyl, pivaloyloxymethyl, 3-sulfopropyl, carbamoylmethyl, 3-carbamoylpropyl, pyrrolidinocarbonylmethyl, 2-(N-ethyl-benzylamino)ethyl, 2-(2-oxopyrrolidino)ethyl, 2-formylaminoethyl, 3-formylaminopropyl, 3-trifluoroacetamido-propyl, 2-benzamino ethyl, 3-tert-butoxycarbonylaminopropyl, benzyloxycarbonylaminopropyl, 2,3-epoxypropyl, 2-thioacetamidoethyl, 3-sulfonaminopropyl, 2-(1,3-dioxoran-2-yl)ethyl, 2-, 3-, 4-pyridylmethyl, 2-(4-pyridyl) ethyl, 3-(4-pyridyl)propyl, furfulyl, 3-(2-furyl)allyl, 3-(2-furyl)propyl, 2-(2-pyranyloxy)ethyl, 2-(3-indolyl)ethyl, 3-(1-indolyl)propyl, 3-(2-benzimidazolyl)propyl, 2-morpholinoethyl, (3-isoxazolyl)methyl, 2-(2-pyridylthio)-ethyl, 2-(2-benzthiazolyl)ethyl, 2-(2-pyrimidinylthio)-ethyl, 2-(2-aminoethylthio)ethyl, 2-isonicotinoylamino-ethyl, 2-thenoylaminoethyl, 2-furoylaminoethyl, 3-(tert-butoxycarbonyloxy)propyl, 2-methylsulfonyloxyethyl, 2-(p-toluenesulfonyloxy)ethyl, 2-(tert-butyldimethylsilyloxy)-ethyl, sulfoaminomethyl, 2-sulfoaminoethyl, ureidomethyl, 2-ureidoethyl, sulfamoylaminomethyl, 2-sulfamoylaminoethyl, 4-methoxybenzyloxycarbonylamino, 4-nitrobenzyloxycarbonyl-amino, 4-chlorobenzyloxycarbonylamino, toluenesulfonylamino, trifluoromethanesulfonylamino, 2-chloroethane-sulfonylamino and 2,2,2-trifluoromethanesulfonylamino.

The substituted or unsubstituted aliphatic hydrocarbon groups, represented by $R_2$ or $R_2.$ also include the same groups as with $R^1$.

When $R_1$ and $R_2$ form a heterocyclic group together with a nitrogen atom, a carbon chain of 3 to 6 carbon atoms such as trimethylene, tetramethylene, pentamethylene or hexamethylene is used for formation of the group. Examples of the groups include azetidino(trimethyleneimino), pyridino (tetramethyleneimino), piperidino(pentamethyleneimino), hexamethyleneimino.

In the above-mentioned formulae, the acyl groups of the substituted or unsubstituted acyl groups, represented by $R_3$, $R_{11}$, $R_{13}$ or $R_{17}$, or the acyl groups in the substituted or unsubstituted acyloxy groups, represented by $R_8$ include carboxylic acyl, sulfonic acyl, phosphorous acyl and phosphoric acyl.

The carboxylic acyl group means an acyl group derived from a carboxylic acid, which may be either a monocarboxylic acid or a polycarboxylic acid, and either a saturated carboxylic acid or an unsaturated carboxylic acid.

Preferred examples of the monocarboxylic acyl groups include saturated or unsaturated acyl groups of 1 to 20 carbon atoms (such as formyl, acetyl, propionyl, butyryl, isobutyryl, valeryl, isovaleryl, hexanoyl, pivaloyl, lauroyl, myristoyl, palmitoyl, stearoyl, acryloyl, propioloyl and methacryloyl) and aryl carboxylic acyl groups. The aryl carboxylic acyl groups include benzene- carboxylic acid and naphthalenecarboxylic acid.

Preferred examples of the polycarboxylic acyl groups include dicarboxylic acyl groups. The dicarboxylic acyl groups include saturated or unsaturated acyl groups of 2 to 6 carbon atoms which may optionally be esterified, such as oxalo, carboxyacetyl, 3-carboxypropionyl, cis-3-carboxyacryloyl, trans-3-carboxyacryloyl and cis-3-methyl-carboxyacryloyl.

The sulfonic acyl group means an acyl group derived from a sulfonic acid. Examples thereof include alkyl-, aryl- and aralkylsulfonic acyl groups. The alkyl group preferably contains, for example, linear or branched alkyl of 1 to 6 carbon atoms. Concrete examples of the alkyl groups include methyl, ethyl, propyl, isopropyl, butyl, isobutyl, sec-butyl, tert-butyl, n-pentyl and n-hexyl. Examples of the aryl groups include phenyl and naphthyl. The aryl groups may have substituents, and examples of the substituents include lower alkyl (for example, methyl), lower alkoxy (for example, methoxy), halogen (for example, fluorine, chlorine and bromine), nitro and carboxy. Examples of the aralkyl groups include 2-phenethyl.

The phosphorous acyl group means an acyl group derived from phosphorous acid. Examples thereof include phosphorous acyl groups obtained from alkyl, aryl and aralkyl derivatives of phosphorous acid. The alkyl group preferably contains, for example, 1 to 6 carbon atoms which may be linear or branched. Concrete examples of the alkyl groups include methyl, ethyl, propyl, isopropyl, butyl, isobutyl, sec-butyl, tert-butyl, n-pentyl and n-hexyl. Examples of the aryl groups include phenyl, tolyl and naphthyl. Examples of the aralkyl groups include arylalkyl, wherein the aryl is preferably the above-mentioned aryl, while the alkyl preferably contains 1 to 3 carbon atoms and includes, for example, methyl, ethyl or propyl.

The phosphoric acyl group means an acyl group derived from phosphoric acid. Examples thereof include phosphoric acyl groups obtained from alkyl, aryl and aralkyl derivatives of phosphoric acid. The alkyl, aryl and aralkyl have the same meanings as with phosphorous acid.

Examples of the substituents in the substituted or unsubstituted acyl groups, represented by $R_3$, $R_{11}$, $R_{13}$ or $R_{17}$ include halogen, alkoxy and alkylthio.

Examples of the halogen atoms include chlorine, bromine, fluorine and iodine.

The alkoxy groups include ones having 1 to 4 carbon atoms such as methoxy, ethoxy, propoxy and butoxy.

The alkylthio groups include ones having 1 to 4 carbon atoms such as methylthio, ethylthio, propylthio, isopropylthio, butylthio, isobutylthio, sec-butylthio and tert-butylthio.

The lower carboxylic acyl groups represented by $R_{12}$ in the above-mentioned formula include monocarboxylic acyl and polycarboxylic acyl of 1 to 6 carbon atoms such as formyl, acetyl, propionyl, butyryl, isobutyryl, valeryl, isovaleryl, hexanoyl, oxalo, carboxyacetyl and 3-carboxypropionyl.

In the above-mentioned formulae, the alkyl groups in the substituted or unsubstituted alkoxy groups, represented by $R_8$ and the alkyl groups of the substituted or unsubstituted alkyl groups, represented by $R_{11}$, $R_{13}$ or $R_{17}$ preferably contain 1 to 3 carbon atoms, and may be linear or branched. Concrete examples of the alkyl groups include methyl, ethyl, propyl and isopropyl. As the substituents, alkoxy of 1 to 3 carbon atoms or alkoxyalkoxy of 2 to 6 carbon atoms is preferred. Examples of the alkoxy groups include methoxy, ethoxy and propoxy, and examples of the alkoxyalkoxy groups include methoxyethoxy, methoxypropoxy, methoxybutoxy, methoxypentyloxy, ethoxyethoxy, ethoxypropoxy, ethoxybutoxy and propoxypropoxy.

In the above-mentioned formula, the alkyl groups of the alkyl groups which may have alkylthio groups as substituents, represented by $R_{12}$, include the above-described alkyl groups. The alkylthio groups as the substituents include lower alkylthio. The lower alkyl group preferably contains 1 to 3 carbon atoms, and examples thereof include methyl, ethyl and propyl.

In the above-mentioned formula, the alkyl groups represented by $R_{14}$ include ones having 1 to 6 carbon atoms. The alkyl groups of 1 to 3 carbon atoms are preferred among others, and concrete examples thereof include methyl, ethyl and propyl.

In the above-mentioned formula, the aryl groups represented by $R_{14}$ include phenyl, tolyl and naphthyl.

In the above-mentioned formula, the alkyl groups represented by $R_{15}$ or $R_{16}$ may be linear or branched, and include ones having 1 to 6 carbon atoms. Concrete examples thereof include methyl, ethyl, propyl, isopropyl, butyl, isobutyl, sec-butyl, tert-butyl, n-pentyl and n-hexyl. The alkyl groups of 1 to 3 carbon atoms are preferred among others, and may be either linear or branched. Examples of the alkyl groups include methyl, ethyl, propyl or isopropyl.

In the above-mentioned formula, the carbon chains represented by $R_{15}$ and $R_{16}$ which form cyclic alkyl groups together with the adjacent carbon atom in the acetal bonds include ones having 4 or 5 carbon atoms such as tetramethylene and pentamethylene.

In the above-mentioned formula, examples of the aryl groups represented by $R_{15}$ or $R_{16}$ include phenyl, tolyl and naphthyl.

In the above-mentioned formula, the dialkylamino groups represented by $R_{15}$ or $R_{16}$ include lower dialkylamino groups, and the lower alkyl groups thereof include ones having 1 to 3 carbon atoms such as methyl, ethyl and propyl.

—A— is preferably represented by formula [2].

Preferred examples of 6,9-hemiacetal-eyrthromycin derivatives having a hydroxyl group at at least one of the 14- and 15-positions of the present invention are represented by the general formula [20]:

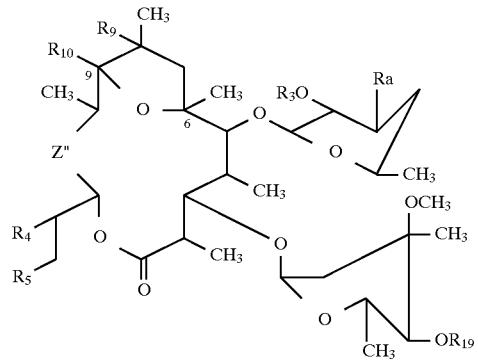
[20]

wherein $R_3$ is selected from the group consisting of:
   a hydrogen atom,
   an acyl radical of $C_{1-5}$ aliphatic carboxylic acid,
   a $C_{6-12}$ aroyl radical,
   a $C_{2-12}$ dialkyloxyphosphoryl radical, and
   a $C_{12-24}$ diaryloxyphosphoryl radical;
$R_4$ and $R_5$ represent hydrogen or hydroxyl group, at least one of $R_4$ and $R_5$ is a hydroxyl group;
$R_{19}$ is selected from the group consisting of:
   a hydrogen atom,
   a $C_{1-6}$ alkanoyl radical which may be substitited by a $C_{1-3}$ alkoxycarbonyl radical,
   a $C_{6-12}$ aroyl radical,
   a $C_{1-6}$ alkylsulfonyl radical,
   a $C_{6-12}$ arylsulfonyl radical,
   a $C_{7-20}$ aralkylsulfonyl radical, and
   a $C_{1-3}$ alkyl radical which may be substituted by $C_{2-6}$ alkoxy radical;
wherein $R_9$ and $R_{10}$ each represent a hydrogen atom or both taken together to form a chemical bond;
wherein Z" stands for the formula:

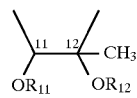
[21]

wherein $R_{11}$ is selected from the group consisting of:
   a hydrogen atom,
   a $C_{1-6}$ alkanoyl radical,
   a $C_{6-12}$ aroyl radical,
   a $C_{1-6}$ alkylsulfonyl radical
   a $C_{6-12}$ arylsulfonyl radical,
   a $C_{7-20}$ aralkylsulfonyl radical, and
   a $C_{1-3}$ alkyl radical which may be substituted by $C_{1-4}$ alkylthio radical,
and $R_{12}$ is selected from the group consisting of:
   a hydrogen atom,
   a $C_{1-6}$ alkanoyl radical; and
   a $C_{1-3}$ alkyl radical which may be unsubstituted by $C_{1-4}$ alkylthio radical,
or wherein Z" stands for the formula:

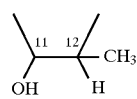
[22]

or Z" stands for the formula:

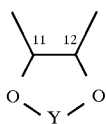
[23]

wherein Y stands for the formula B—$R_{14}$, (wherein $R_{14}$, stands for $C_{6-12}$ aryl radical), >C=O, >S=O, C=S, or Y stands for the formula. [24]:

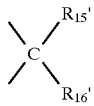
[24]

wherein each of $R_{15}$, and $R_{16}$, which may be the same or different, stands for a hydrogen atom or a $C_{1-6}$ alkyl radical; $R_a$ stands for the formula [25]:

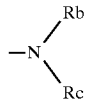
[25]

wherein $R_b$ is selected from the group consisting of:

a hydrogen atom and a $C_{1-6}$ alkyl radical:

and wherein $R_c$ is selected from the group consisting of:

a hydrogen atom, a $C_{2-6}$ alkyl radical which may be substituted with one or more hydroxyl radicals, a C2-6 alkynyl radical;

or together $R_b$ and $R_c$ from a $C_{3-6}$ cyclic alkylamino radical together with the adjacent nitrogen atom; or $R_a$ stands for the formula [26]:

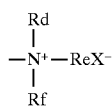
[26]

wherein $R_d$ is $C_{1-6}$ alkyl radical, and $R_e$ and $R_f$, which may be the same or different are selected from the group consisting of:

a hydrogen atom a $C_{1-6}$ alkyl radical which may be substituted by hydroxyl radical, carboxy radical, cyano radical, or halogen, a $C_{3-5}$ cycloalkyl radical, or a $C_{1-3}$ alkoxycarbonyl radical;

a $C_{7-20}$ aralkyl radical;

a $C_{2-6}$ alkenyl radical; and a $C_{2-6}$ alkynyl radical; or together $R_e$ and $R_f$ form a $C_{5-7}$ cyclic alkylamino radical with the adjacent nitrogen atom; and $X^-$ stands for an anion.

Most preferred examples of 6,9-hemiacetal-erythromycin derivatives having a hydroxyl group at at least one of the 14- and 15-positions of the present invention are represented by the general formula [27]:

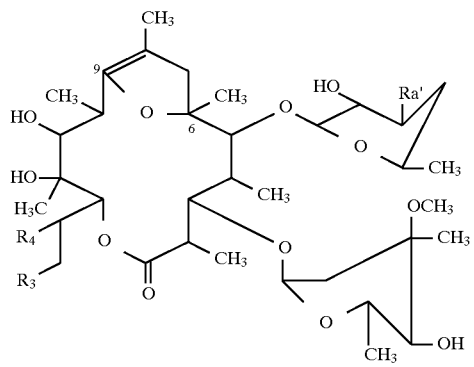
[27]

wherein $R_4$ and $R_5$ represent hydrogen or hydroxyl group, at least one of $R_4$ and $R_5$ is a hydroxyl group, $R_a$, stands for the formula:

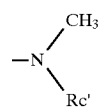
[28]

wherein R, is ethyl or isopropyl, or $R_a$, stands for the formula:

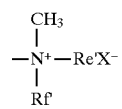
[29]

wherein $R_e$, and $R_f$, which may be the same or different, are selected from the group consisting of methyl, ethyl and isopropyl radicals, each of which may be either unsubstituted or substituted by radicals selected from the group consisting of hydroxyl, cyano, halogen, cyclopropyl and propargyl; or together $R_e$, and $R_f$, form a pyrrolidino or piperidino ring with the adjacent nitrogen atom; and X stands for a halogen anion.

In the present invention, preferred examples of the 6,9-hemiacetal-erythromycin derivatives having hydroxyl groups at at least one of the 14- and 15-positions or the salts thereof include compounds in which $R_1$ is methyl, $R_2$ is isopropyl or ethyl, $R_{18}$ is hydrogen or a hydroxyl group, $R_7$ is methyl and $R_8$, is hydroxyl in the formula [11].

Concrete examples of these preferred compounds include N-demethyl-15-hydroxy-N-isopropyl-8,9-anhydroerythromycin A 6,9-hemiacetal, N-demethyl-14-hydroxy-N-isopropyl-8,9-anhydorerythromycin A 6,9-hemiacetal, 3'-O-demethyl-N-demethyl-14-hydroxy-N-isopropyl-8,9-anhydroerythromycin A 6,9-hemiacetal, N-demethyl-15-hydroxy-N-ethyl-8,9-anhydroerythromycin A 6,9-hemiacetal, N-demethyl-14-hydroxy-N-ethyl-8,9-anhydroerythromycin A 6,9-hemiacetal and 3'-O-demethyl-N-demethyl-14-hydroxy-N-ethyl-8,9-anhydroerythromycin A 6,9-hemiacetal.

The present invention will be described further according to the following formula ([12] and Table 1.

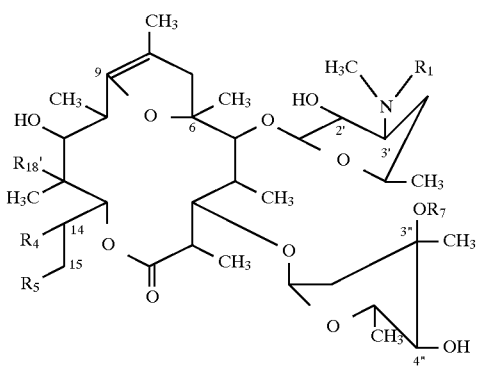

[12]

TABLE 1

| Compound No. | $R_1$ | $R_{18'}$ | $R_4$ | $R_5$ | $R_7$ |
|---|---|---|---|---|---|
| (1)* | Isopropyl | OH | H | H | Methyl |
| (2)* | Ethyl | OH | H | H | Methyl |
| (3) | Isopropyl | OH | H | OH | Methyl |
| (4) | Isopropyl | OH | OH | H | Methyl |
| (5) | Isopropyl | OH | OH | H | H |
| (6) | Isopropyl | OH | H | H | H |
| (7) | Ethyl | OH | H | OH | Methyl |
| (8) | Ethyl | OH | OH | H | Methyl |
| (9) | Ethyi | OH | OH | H | H |

*(1), (2): starting compound

First, the present inventors examined whether or not metabolites promoting the gastrointestinal motor (having GMS activity) were formed in vivo when the compound (1) or (2), the 6,9-hemiacetal-erythromycin derivative known in the art, was given to the animal.

The lactobionate of the compound (1) (10 mg/kg, iv) was injected into the fore-limb of the dog, and the blood, the liver, the bile and the urine were subjected to HP-20 chromatography. After extraction with ethyl acetate, active metabolites were determined. At least two metabolites exhibited GMS activity, and were present in the liver and also considerably present in the urine and the bile. The original compound was largely present in the blood. The liver was collected 30 minutes after administration, and an extracted concentrated solution thereof was subjected to HP-20 chromatography. The 80% v/v methanol/0.005N HCl fraction was extracted with ethyl acetate, and then, the extract was concentrated to obtain a powder. This powder was subjected to fractional HPLC to obtain two active fractions (fractions each containing the compounds (3) and (4)). These exhibited a single peak on three-dimensional HPLC, and showed m/z 760 ($MH^+$), 602 (MH-Cladinose) in FAB mass spectrum (FAB-MS).

The lactobionate of the compound (2) was treated in a manner similar to that described above to obtain the compounds (7) and (8).

The compounds (3), (4), (7) and (8) have the appearance of white powder and basic fat-soluble properties. The physicochemical properties of these compounds are as shown in examples.

The structural formulae of these compounds were determined by analyzing the data of the proton-proton two-dimensional correlation spectrum ($^1H$—$^1H$ COSY), a kind of NMR spectrum, in detail. Namely, it has become clear that the compounds (3) and (4) are the 15- and 14-hydroxyl derivatives of the compound (1), respectively, and that the compounds (7) and (8) are the 15- and 14-derivatives of the compound (2), respectively.

Methods for obtaining the 6,9-hemiacetal-erythromycin derivative of the present invention (see the formula [1] [11] and [16], hereinafter occasionally referred to as a desired compound of the present invention) or the salt thereof of the present invention include, for example, the method of subjecting the 6,9-hemiacetal-erythromycin derivative (see the formula [14], [15] and [17], hereinafter occasionally referred to as a starting compound of the present invention) or the salt thereof to oxidation reaction.

The oxidation reaction is conducted, for example, by use of oxidases derived from organisms. The oxidases used derived from organisms include oxidases derived from the livers of mammals (for example, dogs, cattle, pigs, guinea pigs and rats).

The oxidases are used as enzymes themselves or enzyme solutions. As the enzyme solutions, for example, homogenates prepared by disrupting the livers and suspending the tissues in buffers having an appropriate concentration are used as such, or crude enzymes obtained by centrifuging the homogenates, and then adding acetone, etc. to the supernatants, followed by pulverization are used.

When the oxidases are allowed to react, coenzymes, dehydrogenases and inorganic salts are preferably used in combination.

Examples of the coenzymes include coenzymes usually used in oxidation-reduction reaction such as nicotinamide adenine dinucleotide ($NAD^+$), its phosphate ($NADP^+$) and reduced products thereof (NADH and NADPH).

Examples of the dehydrogenases include D-glucose 6-phosphate dehydrogenase and glycerol 3-phosphate dehydrogenase.

Examples of the inorganic salts include alkaline earth metal halides such as magnesium chloride.

The concentration of the starting compounds on reaction is about 5 μg/ml to about 5 mg/l, and preferably about 20 μg/ml to about 2 mg/ml. The reaction temperature is about 30 to 42° C., and preferably about 34 to 40° C. The reaction time is about 5 minute to 24 hours, and preferably about 10 minutes to 20 hours.

The desired compounds of the present invention or the salts thereof are obtained by allowing the microorganism-derived oxidases to react with the starting compounds of the present invention or the salts thereof.

The microorganisms have the ability to oxidize the 6,9-hemiacetal-erythromycin derivatives, the starting compounds of the present invention. Examples of such microorganisms include strains belonging to actinomycetes. Of these, for example, strains belonging to Amycolatopsis (according to the IFO list in 1992, Streptomyces in the IFO list in 1988), Saccharothrix (according to the IFO list in 1992, Nocardia in the IFO list in 1988) or Dactylosporangium are preferred. Typical examples of the strains include *Amycolatopsis tolypophorous* IFO 13151 (according to the IFO list in 1992, *Streptomyces tolypophorus* in the IFO list in 1988), *Saccharothrix mutabilis* subsp. *capreolus* IFO 12847 (according to the IFO list in 1992, *Nocardia capreola* IFO 12847 in the IFO list in 1988) and Dactylosporangium variesporumIFO 14104. The IFO numbers are deposit numbers with the institute for Fermentation, Osaka, Japan (IFO).

These actinomycetes can be mutated, for example, by irradiation with ultraviolet light, X-rays, radiations or the like, single spore isolation, various mutation processes or other procedures, in a manner similar to that of other actinomycetes. It is unnecessary to substantially distinguish between such mutants and naturally occurring mutants as different species, in comparison of taxonomic properties, and all microorganisms having ability to oxidize the starting compounds of the present invention can be utilized in the present invention.

Media used for cultivation of these microorganisms may be liquid or solid, as long as they contain nutrients which can be utilized by the microorganisms. When the microorganisms are cultivated in large amounts, the liquid media are preferably used.

To the media are appropriately added carbon sources, nitrogen sources, inorganic materials and micronutrients which are anabolizable with the microorganisms. Examples of the carbon sources include glucose, lactose, sucrose, maltose, dextrin, starch, glycerin, mannitol, sorbitol, fats and oils (for example, soybean oil, lard oil and chicken oil) and n-paraffin. Examples of the nitrogen sources include meat extract, yeast extract, soybean powder, corn steep liquor, peptone, cotton seed oil, blackstrap molasses, urea and ammonium salts (for example, ammonium sulfate and ammonium chloride). Further, salts including sodium, potassium, calcium, magnesium and the like, metal salts of iron, manganese, zinc, cobalt, nickel and the like, salts of phosphoric acid, boric acid and the like, salts of organic acids such as acetic acid, propionic acid and oxalic acid are appropriately used. In addition, amino acids (for example, glutamic acid, aspartic acid, alanine, lysine, methionine and proline), peptides (for example, dipeptides and tripeptides), vitamins (for example, vitamin $B_1$, vitamin $B_2$, vitamin $B_6$, nicotinic acid, vitamin $B_{12}$ and vitamin C) and nucleic acids (for example, purine, pyrimidine and derivatives thereof) may be added.

In order to adjust the pH of the media, inorganic acids (hydrochloric acid, sulfuric acid, nitric acid, phosphoric acid and boric acid), organic acids (for example, acetic acid, oxalic acid, citric acid and tartaric acid), alkalis (for example, sodium hydroxide, potassium hydroxide and sodium carbonate) or buffers (for example, sodium dihydrogenphosphate and disodium hydrogenphosphate) may be added. For the purpose of defoaming, fats and oils (for example, soybean oil, lard oil and chicken oil) or surface active agents may also be added in appropriate amounts.

For example, in case of liquid cultivation, it is preferred that the media have a pH around neutrality, particularly about 5 to 8. The cultivation temperature is preferably about 20 to 37° C. The cultivation time is preferably about 6 to 72 hours, and more particularly about 12 to 48 hours.

By the use of the oxidases of the present invention, for example, one or more of the 14- and 15-positions and the 3"-methyl group of the starting compound (c.f. the formula [14]) are converted to hydroxyl groups.

The oxidases are used as enzymes themselves or enzyme solutions.

As the enzyme solutions, the above-mentioned culture solutions may be used as such, or solutions may be used which contain crude enzymes obtained by centrifuging the culture solutions, and then adding acetone to the supernatants, followed by pulverization. In the present invention, it is preferred that the culture solutions are used.

Further, the enzyme solutions may contain coenzymes such as nicotinamide adenine dinucleotide (NAD$^+$), its phosphate (NADP$^+$) and reduced products thereof (NADH and NADPH), dehydrogenases such as D-glucose 6-phosphate and glycerol 3-phosphate, or inorganic salts such as alkaline earth metal halides (for example, magnesium chloride).

When the starting compounds are added to the enzyme solutions for reaction, the concentration of the starting compounds is preferably about 1 µg/ml to 20 mg/ml, and more preferably about 2 µg/ml to 10 mg/ml. The reaction temperature is preferably about 18 to 42° C., and more preferably about 24 to 37° C. The reaction time is preferably about 1 minute to 50 hours, and more preferably about 5 minutes to 30 hours.

Methods for collecting the desired 6,9-hemiacetal-erythromycin derivatives or the salts thereof from the reaction solutions will be described below.

These compounds are basic and exhibit fat solubility, so that general procedures of natural product chemistry utilizing these properties may be used.

Examples of such procedures include (1) a method in which a filter aid is added to the enzyme reaction solution, the mixture is subjected to filtration or centrifugation to remove solid matters, the pH of the resulting solution is adjusted to about 5 to 11, preferably about 6 to 10, followed by addition of an organic solvent immiscible with water (for example, chloroform, ethyl acetate, methyl isobutyl ketone or isobutanol) to extract the desired compound, the extract is washed with water containing an inorganic material (for example, aqueous-sodium bicarbonate or aqueous sodium carbonate) and water, and the organic solvent layer is concentrated, thereby obtaining a crude product containing the desired compound, and (2) a method for collecting a crude product of the desired compound from the enzyme reaction solution or the filtrate obtained by filtration as described above, using a carrier. In order to elute an active material from the carrier by which the active material in the enzyme reaction solution is absorbed, an appropriate solvent, for example, a mixed solvent of an organic solvent such as acetone, acetonitrile or methanol and water or water containing an appropriate amount of an acid (for example, hydrochloric acid or sulfuric acid), is used. The eluted fractions are treated by the solvent extraction method described above after removal of the organic solvent to obtain the desired product. Concentration of the extract provides the crude material. In the present invention, the method of collecting the crude material of the desired compound from the enzyme reaction solution using the carrier is preferred.

As the carriers, inorganic or organic carriers in common use are employed. Examples thereof include active carbon, absorbing resins, ion exchange resins, alumina, cellulose, ion exchange cellulose, Sephadex and ion exchange Sephadex. Of these, the absorbing resins are preferred. In particular, the absorbing resins such as Diaion HP-20 and SP-207 (Mitsubishi Kasei Corp.) and Amberlite XAD-I and II (Rohm & Haas Inc., U.S.A.) are preferably used.

Further purification of this crude material can provide the pure 6,9-hemiacetal-erythromycin derivative or the salt thereof.

For example, various kinds of chromatography are advantageously used. For example, when column chromatography is conducted, inorganic or organic carriers in common use are used as the carriers. Examples of such carriers include active carbon, absorbing resins, alumina, cellulose, crystalline cellulose, ion exchange cellulose, Sephadex [Sephadex LH-20 (Pharmacia, Sweden)], ion exchange Sephadex and silica gel. The crude material is usually purified by column chromatography. In order to elute the active material from a column, an appropriate organic solvent such as n-hexane, chloroform, toluene, ethyl acetate, dichloroethane, acetone or methanol is used alone or in combination as a mixed solvent.

Fractional high performance liquid chromatography (HPLC) may also be used to further purify the crude material to obtain the pure desired compound. As the carriers, octadecylsilane (hereinafter referred to as ODS) carriers or silica gel carriers are advantageously used. For example, in case of ODS, a mixed solvent of methanol or acetonitrile and a salt-containing aqueous solution is advantageously used as a mobile phase. The eluate containing the desired compound is extracted with an appropriate organic solvent immiscible with water, the extract is concentrated, and the residue is polverized from the above-mentioned appropriate organic solvent, thereby obtaining the pure compound.

The 6,9-hemiacetal-erythromycin derivative having a hydroxyl group at at least one of the 14- and 15-positions of the present invention has an amino group. The derivative can therefore be allowed to react with an acid by known methods per se to form a physiologically acceptable salt. Examples of the acids include organic acids (for example, ethylsuccinic acid, lactobionic acid, oxalic acid, succinic acid, citric acid, lactic acid, acetic acid and methanesulfonic acid) and inorganic acids (for example, sulfuric acid, hydrochloric acid and phosphoric acid).

The above-mentioned 6,9-hemiacetal-erythromycin derivative having a hydroxyl group at at least one of the 14- and 15-positions is subjected to alkylation, alkenylation or alkynylation reaction (quaternary ammoniating reaction), whereby a quaternary salt can be prepared.

Examples of reagents used in the reaction include halides, esters and trioxonium salts of corresponding alkyl, alkenyl or alkynyl.

Examples of halogen in the halides include chlorine, bromine and iodine. Iodine is preferred among others.

Examples of the esters include sulfates.

Concrete examples of the trioxonium salts include trimethyloxonium fluoroborate and triethyloxonium fluoroborate.

The reaction reagent is used in an amount of about 1 to 100 molar equivalent, preferably about 2 to 25 molar equivalent per mol of the starting compound.

Examples of solvents used in the reaction include halogenated hydrocarbons (such as chloroform and dichloromethane), ethers (such as ethyl ether and tetrahydrofuran, esters (such as ethyl acetate) and alcohols (such as methanol and ethanol).

The reaction is carried out under ice cooling (about 0° C.) to the boiling point of the solvent (about 100° C.), preferably at room temperature (about 15 to 25° C.) to about 80° C.

The reaction time is about 2 hours to 1 weeks.

The quaternary ammoniating reaction can be conducted before or after the above-mentioned acylation. In particular, it is preferred that the quaternary ammoniating reaction is conducted after the acylation.

After optional washing with aqueous sodium carbonate or aqueous sodium chloride, drying or concentration, an ether is added to the reaction solution to form a precipitate, which is separated by filtration to isolate a product, thereby obtaining a salt of an anion from the reagent used in the quaternary ammoniating reaction.

When the reaction solution is subjected, for example, to silica gel or ion exchange resin chromatography, using a system in which concentrated aqueous ammonia is added to chloroform-methanol as a developing solvent, a compound with hydroxy (OH⁻) as an anion can be obtained.

The anion of the compound thus obtained can be exchanged with another anion by known methods.

The anions in the quaternary ammonium salts include halogen ions (such as a iodine ion, a bromine ion and a chlorine ion), a sulfate ion, a phosphate ion, a nitrate ion, a methanesulfate ion, a p-tolylsulfonate ion, a benzensulfonate ion, a hydroxyl ion and organic carboxylate ions (such as an oxalate ion, a maleate ion, a fumarate ion, a succinate ion, a citrate ion, a lactate ion, a trifluoroacetate ion, a lactobionate ion, an acetate ion, a propionate ion and an ethylsuccinate ion).

The 6,9-hemiacetal-erythromycin derivatives or the salts thereof, the starting compounds of the present invention, can be obtained by known methods, for example, methods described in the above-mentioned literatures (EP-A-213617, EP-A-215355, and J. Med. Chem., 30, 1941–1943 (1987)).

The 6,9-hemiacetal-erythromycin derivatives having hydroxyl groups at at least one of the 14- and 15-positions or the salts thereof, the desired compounds of the present invention, exhibit a strong gastrointestinal function promoting effect as is shown in the experimental examples described below.

With respect to the lactobionate of the compound (8) of the present invention, no case of death was observed in the acute toxicity test using the mice even in a dosage of 100 mg/kg (intravenous injection).

As described above, the 6,9-hemiacetal-erythromycin derivatives having hydroxyl groups at at least one of the 14- and 15-positions or the salts thereof, the desired compounds of the present invention, have an excellent gastrointestinal function promoting effect, and are low in toxicity. It is therefore useful as gastrointestinal function promoting agents for the purpose of treating abnormalities of digestive function (for example, nausea at the stomach, vomiting and anorexia) of mammals (for example, mice, rats, dogs, cattle, pigs and humans).

The gastrointestinal function promoting agents containing the 6,9-hemiacetal-erythromycin derivatives having hydroxyl groups at at least one of the 14- and 15-positions or the salts thereof, the desired compounds of the present invention, as active ingredients are obtained by mixing the compounds with pharmaceutically acceptable carriers. The agents can be provided in formulation suitable for pharmaceutical drugs, for example, in the form of injections, drops, solutions and suspensions as parenteral agents, and in the form of capsules, tablets, syrups, powders and granules as oral agents.

When the parenteral agents such as injections are produced, they may contain isotonic agents (for example., glucose, sorbitol, mannitol and sodium chloride), preservatives (for example, benzyl alcohol, chlorobutanol and methyl p-hydroxybenzoate), anticoagulants (for example, dextran sulfate and heparin), solubilizers (for example, lactobionic acid compounds, cyclodextrins and Tween) and stabilizers (for example, polyethylene glycol and polylactic acid). In giving the agents, these antibiotics are dissolved in aqueous diluents in common use, and used as solutions. The diluents include aqueous glucose, physiological saline solution, Ringer solution and nutrition feeding agent solution. Further, the oral agents may contain additives such as excipients, binders, disintegrators, lubricants, coloring agents, flavors and stabilizers.

These preparations are given to mammals orally or parenterally. For example, when the preparations are given to humans, the dosage varies depending on the kind and degree of the subject disease, the age of the patients and the like. Usually, an adult patient is given parenterally about 0.1 to 20 mg a day, preferably about 0.2 to 5 mg, and orally about 1 to 100 mg a day, preferably about 2 to 50 mg.

Structural formulae of the starting compounds (the compounds (1) and (2)) and the desired compounds (the compounds (3) to (9)) used in the following examples are summarized in Table 1 shown above.

These compounds were subjected to HPLC using solvent systems shown in Table 2 as mobile phases. The respective retention times are shown in Table 2.

TABLE 2

| Compound No. | | Retention Time (minute) Solvent System | | |
|---|---|---|---|---|
| | | 28% CH$_3$CN | 32% CH$_3$CN | 37% CH$_3$CN |
| Desired | (3) | 7.8 | 4.3 | 2.7 |
| Compound | (4) | 15.5 | 7.7 | 4.1 |
| | (5) | 10.2 | 5.3 | 3.2 |
| | (6) | 30.9 | 14.0 | 6.6 |
| | (7) | 6.4 | 3.6 | 2.4 |
| | (8) | 12.2 | 6.3 | 3.7 |
| | (9) | 8.6 | 4.6 | — |
| Starting | (1) | — | 24.0 | 10.8 |
| Compound | (2) | 42.7 | 18.2 | 8.6 |

Conditions:
Column; ODS (YMC-Pack A 312 S-5, Yamamura Kagaku Kenkyusho)
Mobile phase; 28%, 32% and 37% acetonitrile/0.02M phosphate buffer (pH 4.0)
Detection; UV 214 nm The present invention will be described in more detail with the following examples and experimental examples.

Percentages in media are weight/volume %, and percentages in column chromatography are volume/volume %.

The abbreiviations found in the examples relative to the $^1$H NMR spectrum are explained as follows:

s: singlet, d: doublet, t: triplet, q: quartet, dd: double doublet, m: multiplet, br: broad, J: coupling constant The abbreiviations found in the examples relative to the $^{13}$C NMR spectrum are explained as follows:

s: a quarternary carbon atom, d:CH, t:CH$_2$, q:CH$_3$

Example 1

A dog liver homogenate (10%, 0.01M sodium potassium phosphate buffer, pH 7.4) was centrifuged (10,000 rpm, 10 minutes) at 0° C., and the supernatant (400 ml) was dispensed in 200 ml portions into Erlenmeyer flasks (1.0 liter). Under ice cooling, nicotinamide (1M aqueous solution, 1.0 ml), magnesium chloride (1M aqueous solution, 0.50 ml), glucose 6-phosphate (170 mg), NADP$^+$(23 mg) and glucose 6-phosphate dehydrogenase (100 unit/ml, 100 µl) were in turn added to each of the flasks and mixed. Then, a 20 mg/ml aqueous solution of the lactobionate of the compound (2) (molar ratio 1:1.1, 2.5 ml) was added to each of the flasks, which were stoppered with urethane plugs, followed by mixing with shaking at 37° C. for 2.5 hours. The reaction mixtures were combined and adjusted to pH 5.4, followed by mixing with an ethyl acetate-hexane mixture (2:1, 400 ml). Then, an aqueous layer was separated from an organic layer and a precipitate by centrifugation (10,000 rpm, 10 minutes). The resulting aqueous layer (400 ml, pH 4.4) was adjusted to pH 8.1 to 8.6, and extracted three times with ethyl acetate (200 ml). The resulting ethyl acetate layers were combined, and washed with water (100 ml) and saturated saline (50 ml), followed by drying with sodium sulfate. Then, the solution was concentrated and evaporated to dryness to obtain an oily product (83 mg). The residual aqueous layer (400 ml) and the washing layer (100 ml) were combined, mixed with NaCla (509), adjusted to pH 8.1 to 8.6, and followed by extraction with ethyl acetate (300 ml). The resulting ethyl acetate layer was washed with saturated saline (50 ml), followed by drying with sodium sulfate. Then, the solution was concentrated and evaporated to dryness to obtain an oily product (29 mg).

The crude extracts thus obtained were combined and dissolved in methanol (1.3 ml). The solution was subjected to preparative HPLC [column; ODS, YMC-Pack, D-ODS-5, mobile phase; 28% v/v acetonitrile/0.02M phosphate buffer, pH 4, flow rate; 10 ml/minute], and fractions having an elution capacity of 200 to 240 ml (fractions containing the compound (7)) and fractions having an elution capacity of 365 to 480 ml (fractions containing the compound (8)) were each collected. Each of the resulting solutions was adjusted to pH 7.4, followed by concentration to about 10 ml under reduced pressure.

The concentrated solution of the fractions containing the compound (7) was extracted three times with ethyl acetate (8 ml) while adjusting it to pH 8.1 to 8.6 in the presence of NaCl (2.0 g). The resulting ethyl acetate layers were combined, and washed with saturated saline (6 ml), followed by drying with sodium sulfate. Then, the solution was concentrated and evaporated to dryness to obtain a powder of the compound (7) (2.8 mg).

After adjustment to pH 4.7, the concentrated solution of the fractions containing the compound (8) was washed with an ethyl acetate-hexane mixture (2:1, 8 ml), and then, extracted three times with ethyl acetate (8 ml) while adjusting it to pH 8.1 to 8.6 in the presence of NaCl (2.0 g). The resulting ethyl acetate layers were combined, and washed with semi-saturated saline (6 ml), followed by drying with sodium sulfate. Then, the solution was concentrated and evaporated to dryness to obtain a powder of the compound (8) (4.7 mg).

Figure 2:
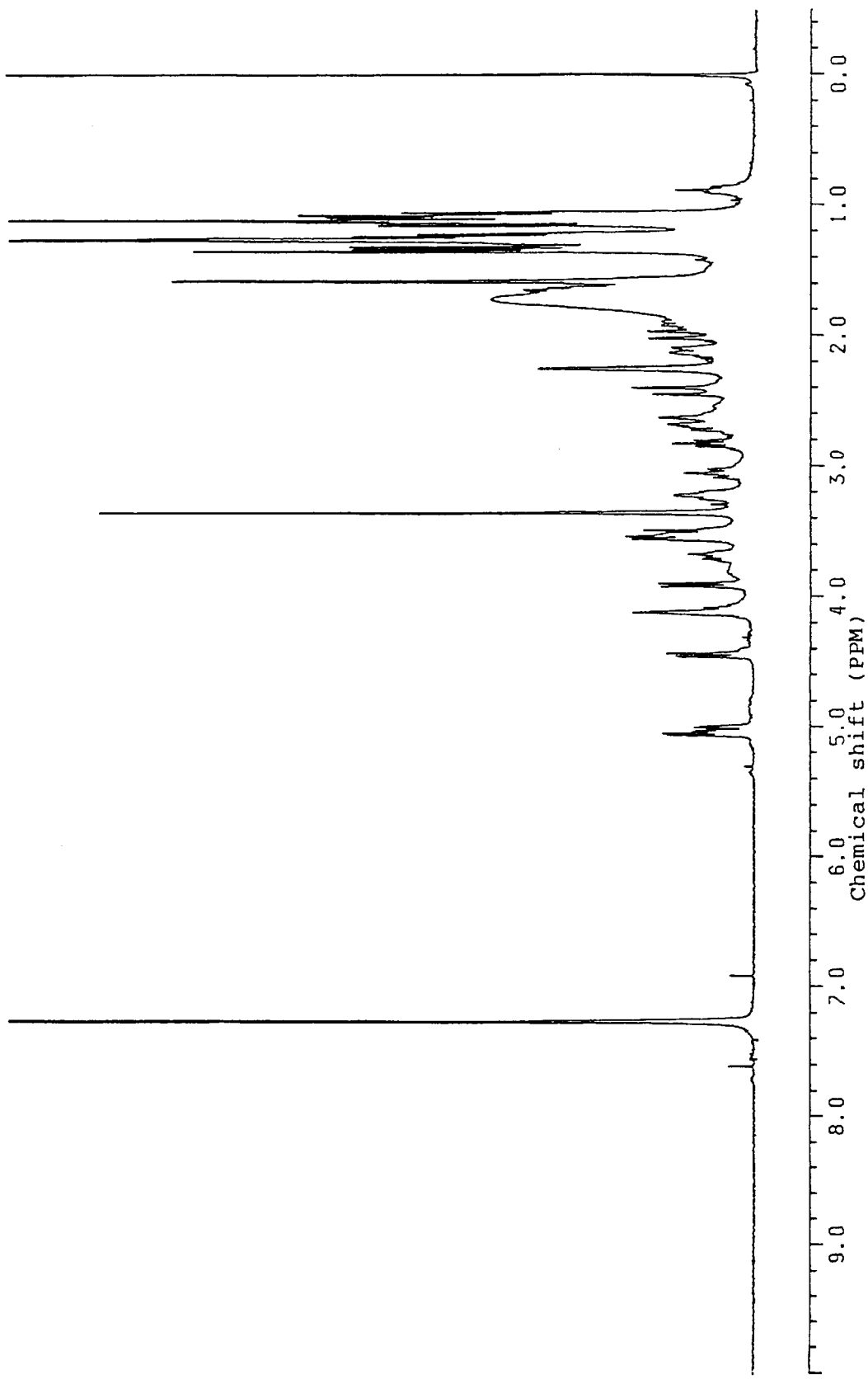
FIG. 2 shows a $^1$H NMR spectrum of the compound (7)

The physicochemical properties of the compounds (7) and (8) are as follows:

Compound (7)
  (1) Molecular weight: m/z 746 (MH$^+$), 588 (MH-Cladinose) (from FAB mass spectrum)
  (2) Molecular formula: $C_{38}H_{67}NO_{13}$
  (3) UV spectrum: in methanol Absorption maximum: 208 nm
  (4) Infrared (IR) absorption spectrum: in KBr [FIG. 1] Main absorption peaks are shown below (wave number, cm$^{-1}$):
    3430, 2970, 2930, 1725, 1630, 1455, 1375, 1200, 1170, 1055, 1010
  (5) $^1$H NMR spectrum: 300 MHz, in CDCl$_3$, δ ppm [FIG. 2] 1.06(3 H, d, J=7.1 Hz), 1.10(3 H, d, J=7.3 Hz), 1.11(3 H, s), 1.14(3 H, d, J=7.4 Hz), 1.23(3 H, d, J=6.1 Hz), 1.26(3H, br), 1.27(3 H, s), 1.33(3 H, d, J=6.2 Hz), 1.35(3 H, s), 1.58(3 H, s), 1.62(2 H, m), 1.91(1 H, dm, J=7.5Hz), 2.00(1 H, d, J=15.6 Hz), 2.11(1 H, brd, J=9.9 Hz), 2.16(1 H, m), 2.25(3 H, brs), 2.42(1 H, d, J=15.3 Hz), 2.60(1 H, brt, J=9.0 Hz), 2.65(1 H, d, J=15.7 Hz), 2.71(1 H, dd, J=7.4, 2.5 Hz), 2.83(1 H, quint, J=7.1 Hz), 3.05(1 H, t, J=9.6Hz), 3.22(1 H, brt, J=8.3 Hz), 3.36(3 H, s), 3.52(1 H, m), 3.53(1 H, m), 3.55(1 H, d, J=7.4 Hz), 3.68(1 H, dt, J=11.6, 4.5 Hz), 3.91(1 H, d, J=7.4 Hz), 4.12(2 H, m), 4.44(1 H, d, J=7.3 Hz), 5.01(1 H, dd, J=9.9, 3.2 Hz), 5.06(1 H, d, J=4.7 Hz)

Figure 3:
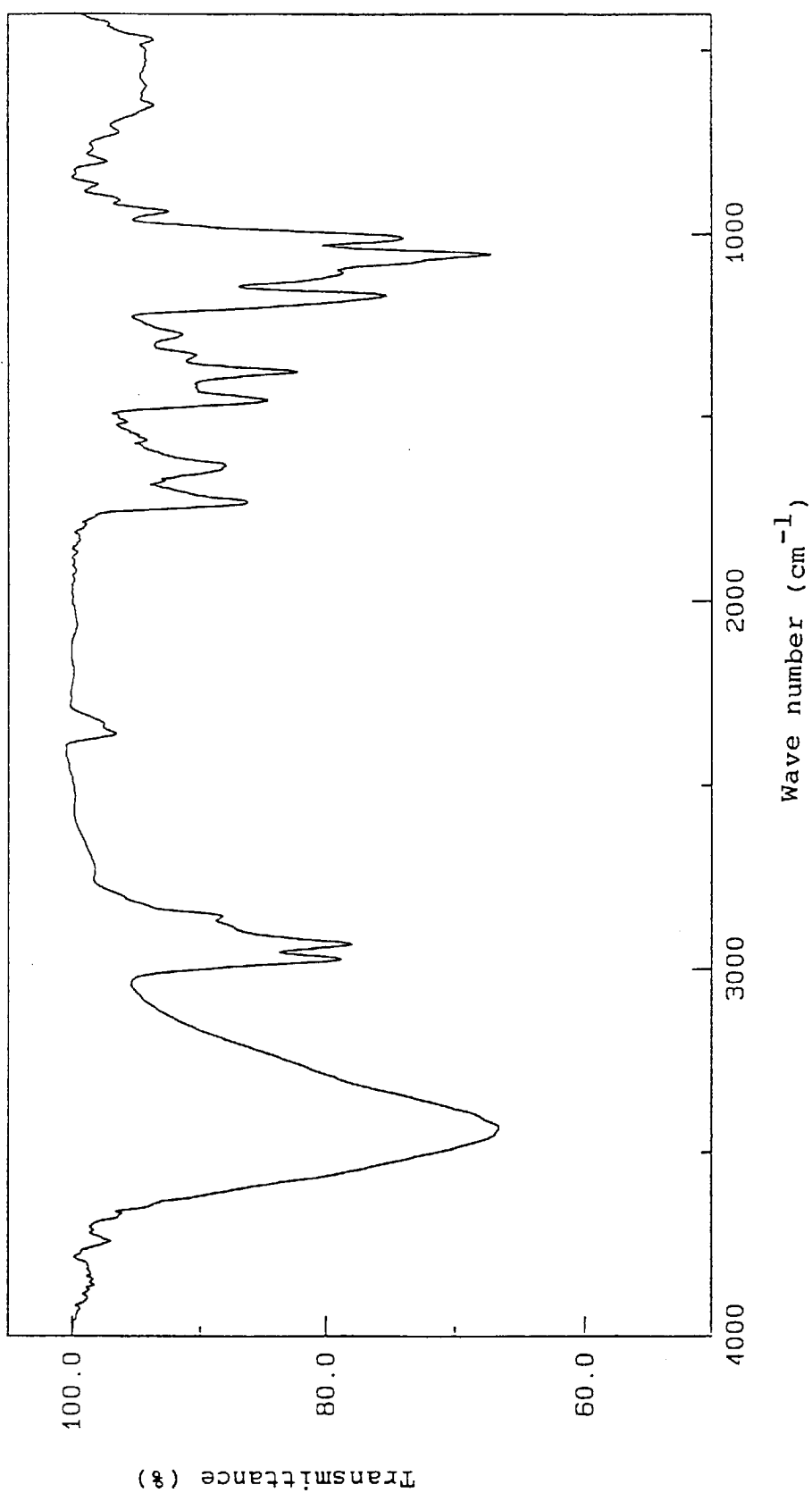
FIG. 3 shows an IR spectrum of a compound (8)
Figure 4:
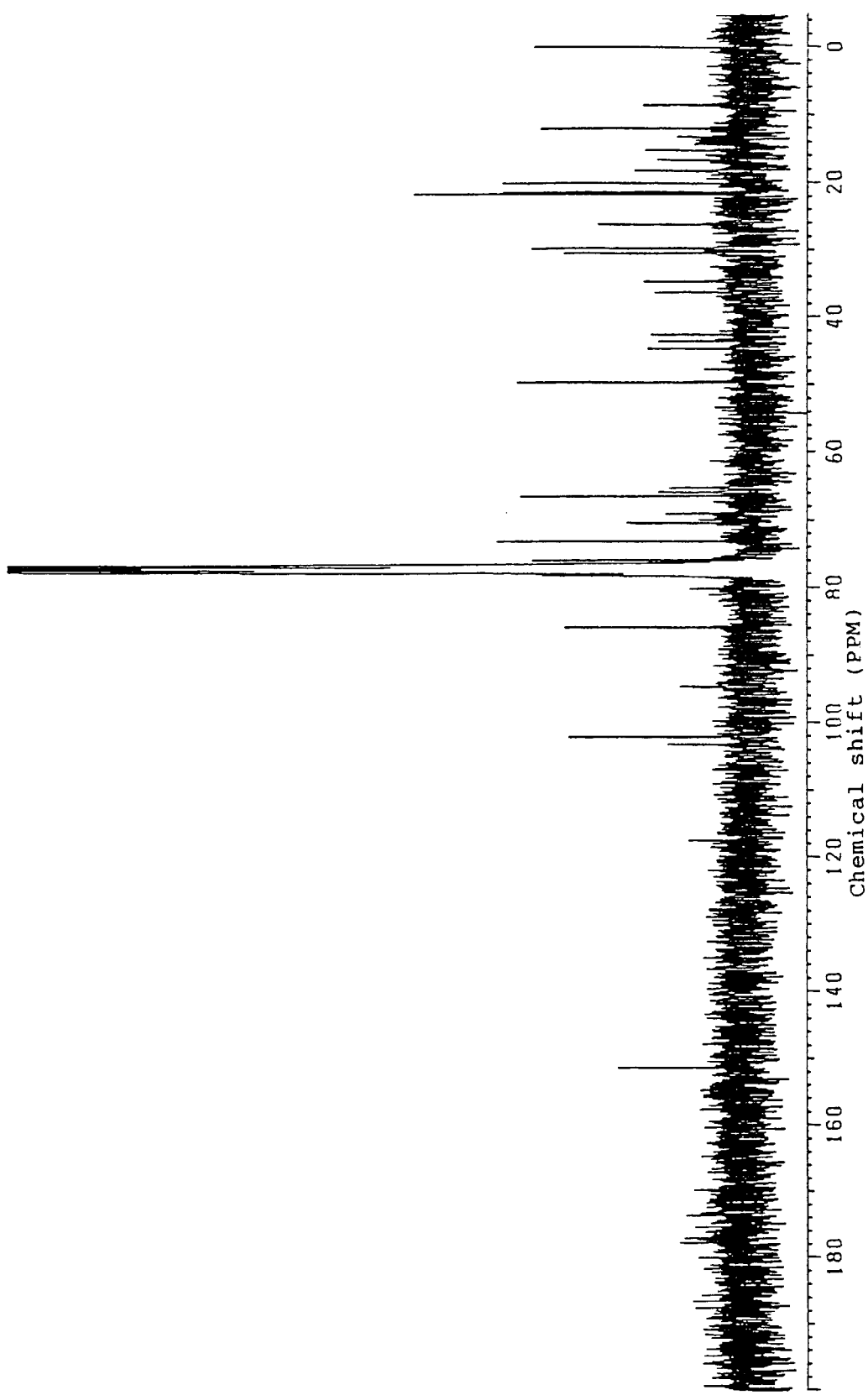
FIG. 4 shows a $^{13}$C NMR spectrum of the compound (8)

Compound (8)
  (1) Molecular weight: m/z 746 (MH$^+$), 588 (MH-Cladinose) (from FAB mass spectrum)
  (2) Molecular formula: $C_{38}H_{67}NO_{13}$
  (3) UV spectrum: in MeOH absorption maximum: 208 nm
  (4) IR spectrum: in a KBr tablet [FIG. 3] Main absorption peaks are shown below (wave number, cm$^{-1}$)
    3430, 2970, 2930, 1730, 1635, 1455, 1375, 1170, 1055, 1010
  (5) $^{13}$C NMR spectrum: 75 MHz, in CDCl$_3$, δ ppm [FIG. 4] 177.5(s), 151.2(s), 103.1(d), 102.0(s), 94.6(d), 85.8

(s), 80.1(d), 78.1(d), 77.2(d), 75.8(d), 73.0(s), 70.3(d), 69.9(d), 69.0(d), 66.4(d), 65.8(d), 65.2(d), 49.6(q), 47.7 (t), 44.6(d), 43.5(d), 42.6(t), 36.3(q), 34.6(t), 30.4(d), 29.7(t), 26.2(q), 21.6(q), 21.3(q), 20.0(q), 18.2(q), 16.6 (q), 15.2(q), 14.4(q), 13.3(q), 12.0(q), 8.6(q)

(6) $^1$H NMR spectrum: 300 MHz, in CDCl$_{31}$, δ ppm 1.06(3 H, d, J=7.0 Hz), 1.09(3 H, d, J=7.4 Hz), 1.10(3 H, d, J=6.1 Hz), 1.14(3 H, d, J=7.5Hz), 1.21(3 H, s), 1.22(3 H, d, J=7.0 Hz), 1.26(3 H,brt,J=7.5 Hz), 1.27(3 H, s), 1.33(3 H,d,J=7.0 Hz), 1.34(3 H, s), 1.39(1 H, m), 1.58(3 H, s), 1.61(1 H, dd, J=15.3, 4.9 Hz), 1.65(1 H, m), 1.86(1 H, td, J=7.2, 2.2 Hz), 1.96(1 H, d, J=15.5 Hz), 2.12(1 H, d, J=9.6 Hz), 2.26(3 H, brs), 2.41(d, J=15.3 Hz), 2.62(1 H, m), 2.64(1 H, d, J=15.7 Hz), 2.69(1 H, dd, J=7.5, 3.0 Hz), 2.78(1 H, quint, J=7.3 Hz), 3.06(1 H, t, J=9.3 Hz), 3.22(1 H, brt, J=8.5 Hz), 3.35(3 H, s),3.42(1 H, d, J=8.2 Hz), 3.54(1 H, m), 3.88(1 H, d, J=7.7 Hz), 4.10(3 H, m), 4.43(1 H, d, J=7.3 Hz), 4.75(1 H, d, J=9.1 Hz), 5.09(1 H, d, J=4.7 Hz)

Example 2

A dog liver homogenate (10%, 0.01M sodium potassium phosphate buffer, pH 7.4) was centrifuged (10,000 rpm, 10 minutes) at 0° C., and the supernatant (1,000 ml) was dispensed in 333 ml portions into Erlenmeyer flasks (1.0 liter). Under ice cooling, nicotinamide (1M aqueous solution, 1.5 ml), magnesium chloride (1M aqueous solution, 0.75 ml), glucose 6-phosphate (255 mg), NADP+ (34 mg) and glucose 6-phosphate dehydrogenase (100 unit/ml, 150 μl) were in turn added to each of the flasks and mixed. Then, a 10 mg/ml aqueous solution of the lactobionate of the compound (1) (molar ratio 1:1.1, 7.5 ml) was added to each of the flasks, which were stoppered with urethane plugs, followed by mixing with shaking at 37° C. for 2.0 hours. The reaction mixtures were combined and adjusted to pH 5.4, followed by mixing with an ethyl acetate-hexane mixture (2:1, 900 ml). Then, an aqueous layer was separated from an organic layer and a precipitate by centrifugation (10,000 rpm, 10 minutes). NaCl (100 g) was added to the resulting aqueous layer (1.0 liter, pH 4.4) and dissolved. The solution was adjusted to pH 8.1 to 8.6, and then extracted three times with ethyl acetate (500 ml). The resulting ethyl acetate layers were combined, and washed with semi-saturated saline (500 ml), followed by drying with sodium sulfate. Then, the solution was concentrated and evaporated to dryness to obtain an oily product (204 mg).

The crude extracts thus obtained were combined and dissolved in methanol (1.0 ml). The solution was subjected to preparative HPLC similar to that of Example 1, and fractions having an elution capacity of 220 to 280 ml (fractions containing the compound (3)) and fractions having an elution capacity of 430 to 620 ml (fractions containing the compound (4)) were each collected. Each of the resulting solutions was adjusted to pH 7.4, followed by concentration to about 10 ml under reduced pressure. Each of these concentrated solutions was extracted three times with ethyl acetate (8 ml) while adjusting it to pH 8.1 to 8.6 in the presence of NaCl (2.0 g). For each of the solutions, the resulting ethyl acetate layers were combined, and washed with semi-saturated saline (6 ml), followed by drying with sodium sulfate. Then, the solutions were concentrated and evaporated to dryness to obtain powders of the compound (3) and the compound (4) (5.8 mg and 6.2 mg).

The physicochemical properties of the compounds (3) and (4) are as follows:

Compound (3)

(1) Molecular weight: m/z 760 (MH$^+$), 602 (MH-Cladinose) (from FAB mass spectrum)

(2) Molecular formula: C$_{39}$H$_{69}$NO$_{13}$ (3) UV spectrum: in methanol, Absorption maximum: 210 nm (ε7,600)

Figure 5:
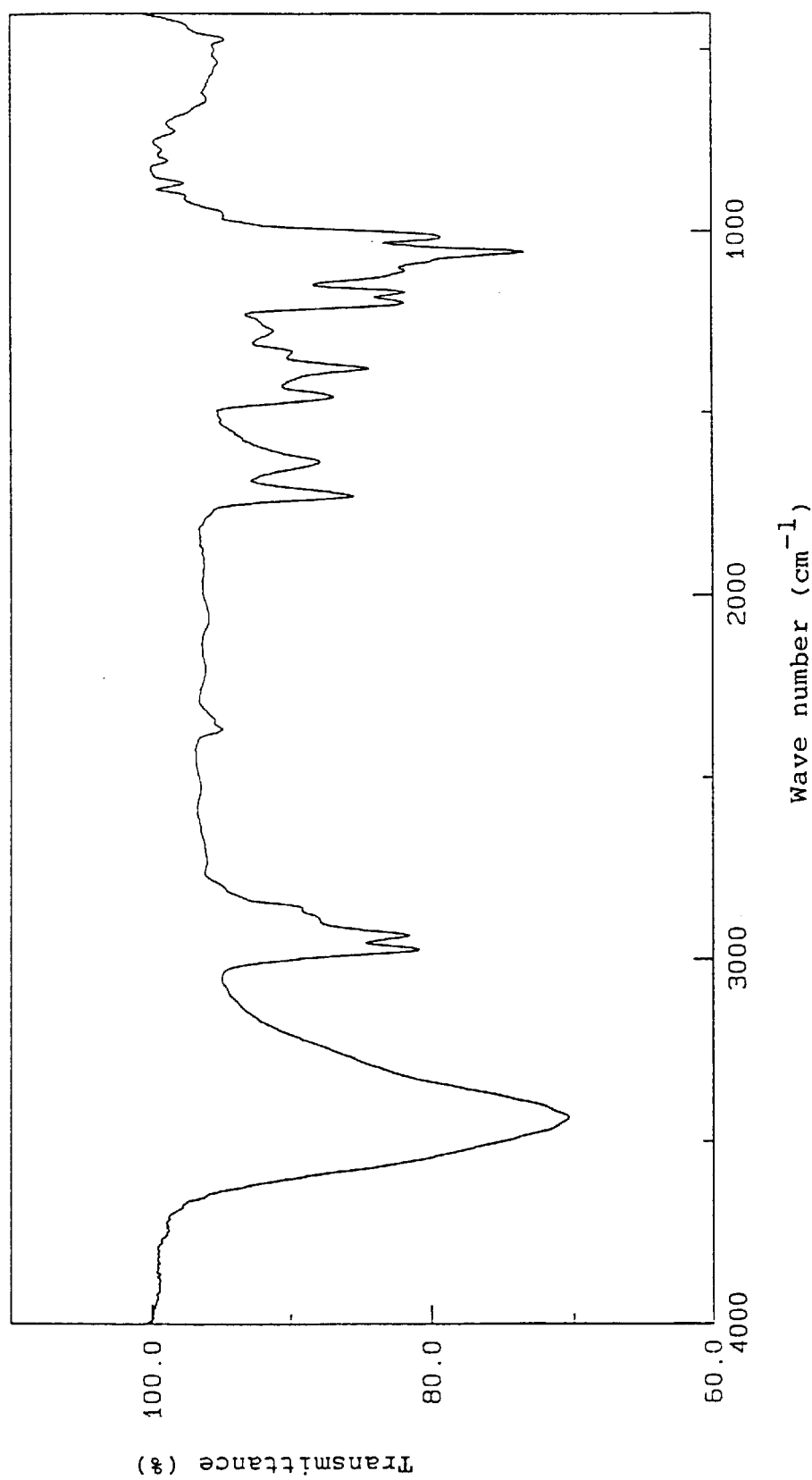
FIG. 5 shows an IR spectrum of a compound (3)

(4) IR spectrum: in a KBr tablet [FIG. 5] Main absorption peaks are shown below (wave number, cm$^{-1}$): 3430, 2970, 2930, 1725, 1635, 1455, 1375, 1195, 1165, 1055, 1010

Figure 6:
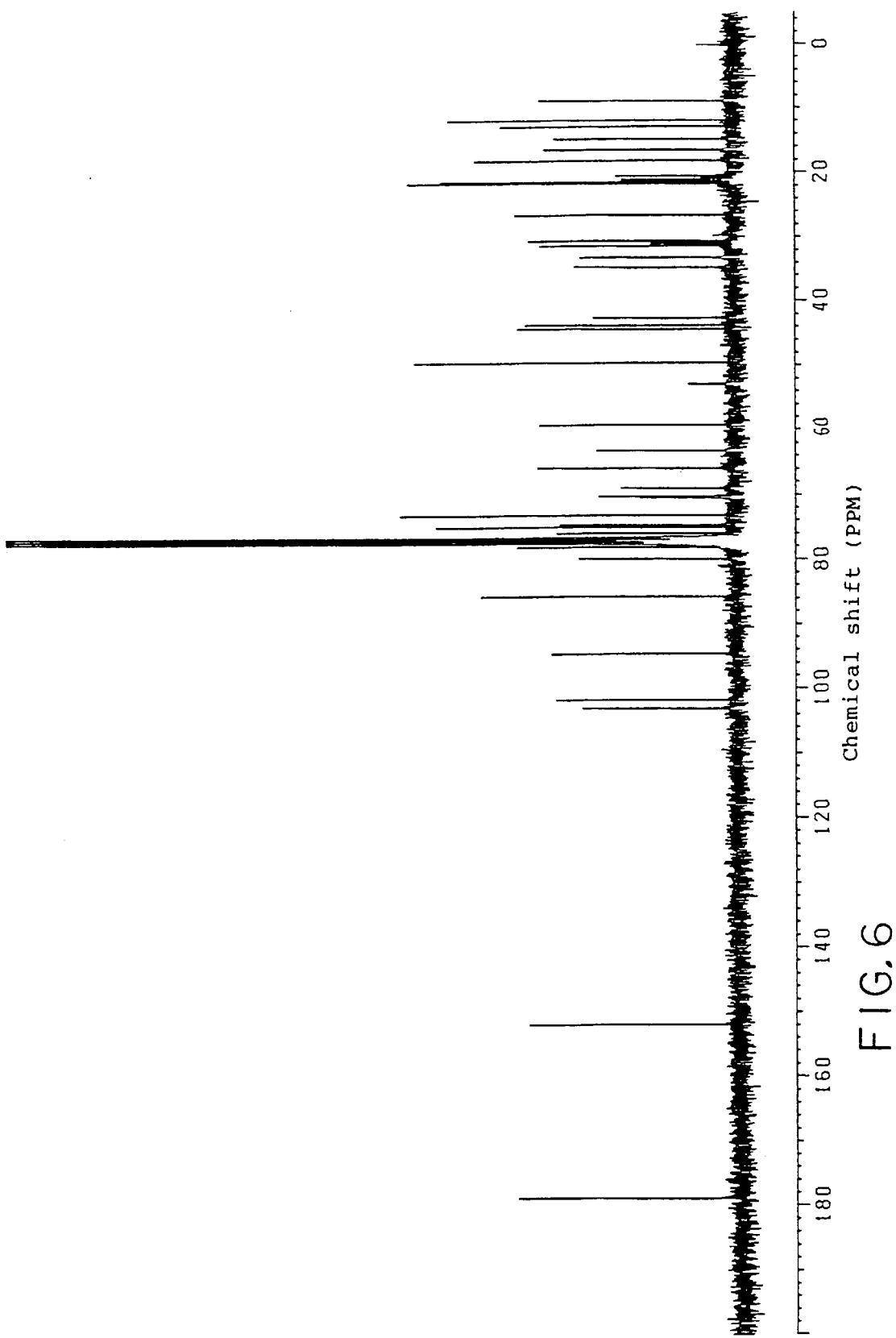
FIG. 6 shows a $^{13}C$ NMR spectrum of the compound (3)

(5) $^{13}$C NMR spectrum: 75 MHz, in CDCl$_3$, δ ppm [FIG. 6] 178.7(s), 151.8(s), 103.0(d), 101.6(s), 94.5(d), 85.6 (s), 79.8(d), 78.1(d), 75.9(d), 74.9(s), 74.6(d), 73.1(s), 70.3(d), 70.2(d), 68.9(d), 65.8(d), 63.1(d), 59.2(t), 52.8 (d), 49.5(q), 44.3(d), 43.7(d), 42.6(t), 34.6(t), 33.1(t), 31.3(t), 30.9(q), 30.5(d), 26.5(q), 21.6(q), 21.4(q), 21.0 (q), 20.5(q), 18.1(q), 16.4(q), 14.7(q), 12.8(q), 11.9(q), 8.8(q)

Compound (4)

(1) Molecular weight: m/z 760 (MH$^+$), 602 (MH-Cladinose) (from FAB mass spectrum)

(2) Molecular formula: C$_{39}$H$_{69}$NO$_{13}$ (3) UV spectrum: in methanol, maximum value: 210 nm (ε8,000)

Figure 7:
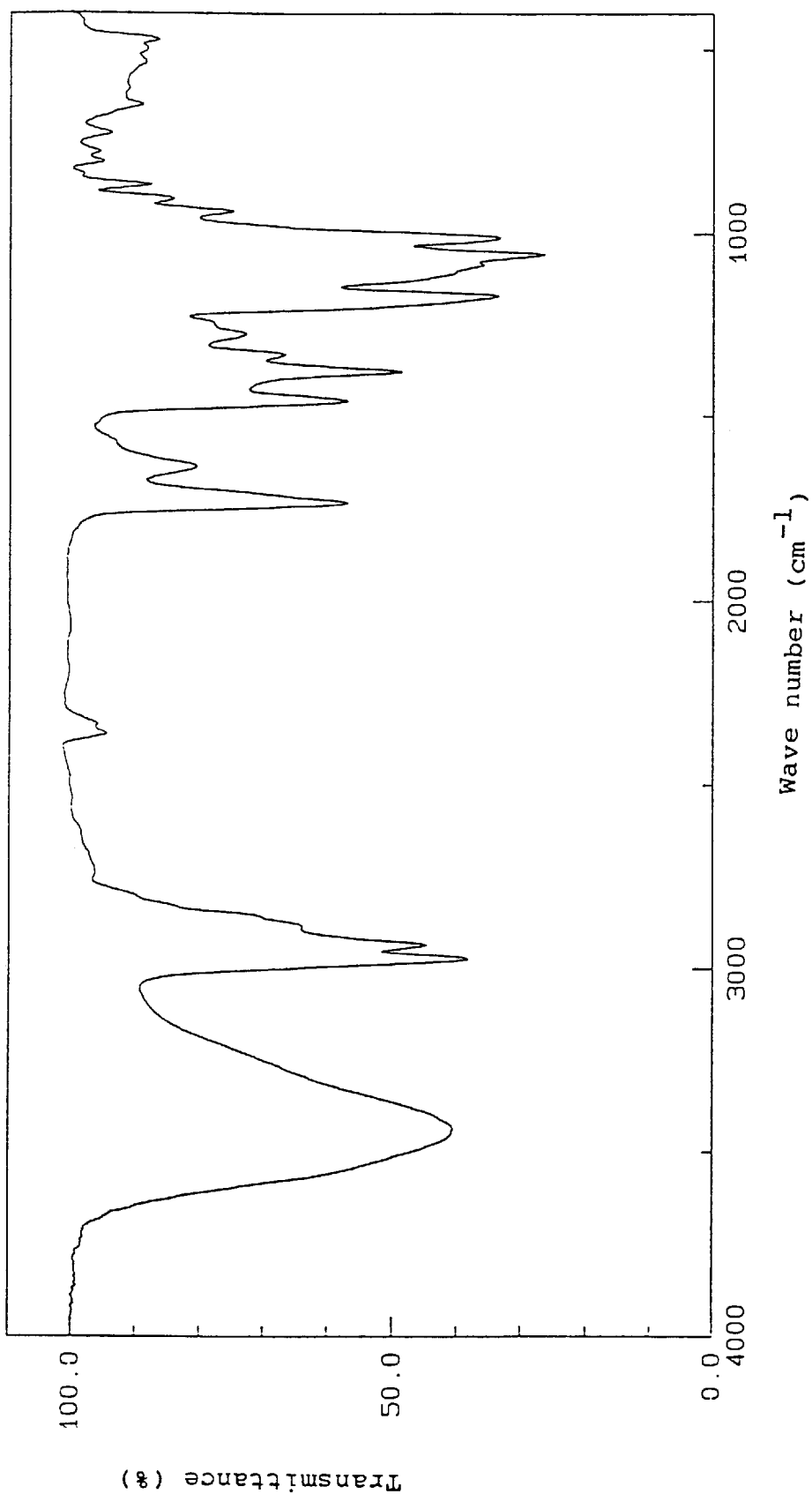
FIG. 7 shows an IR spectrum of a compound (4)

(4) IR spectrum: in a KBr tablet [FIG. 7] Main absorption peaks are shown below (wave number, cm$^{-1}$): 3435, 2970, 2935, 1730, 1635, 1460, 1375, 1170, 1055, 1010

Figure 8:
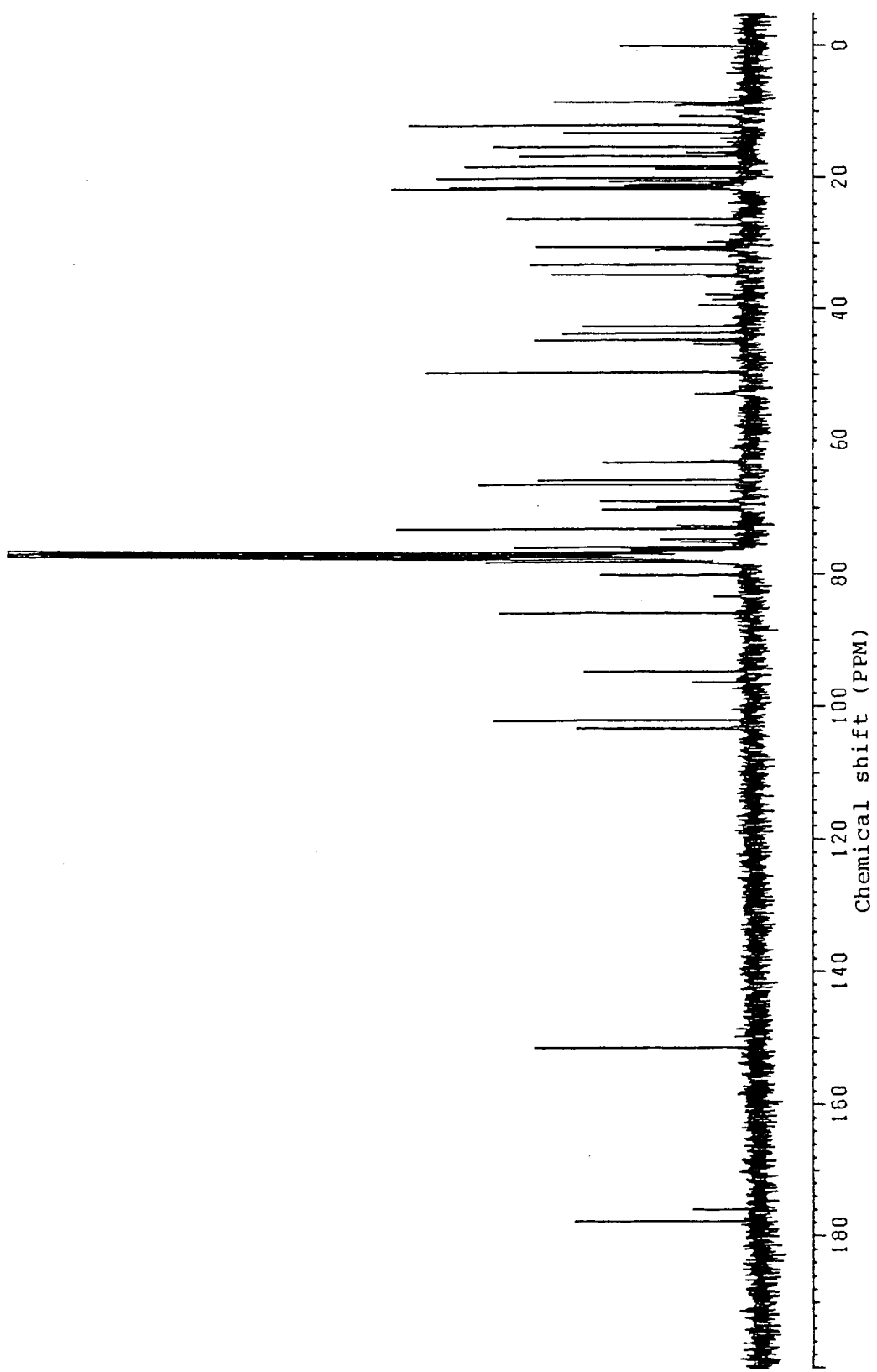
FIG. 8 shows a $^{13}C$ NMR spectrum of the compound (4)

(5) $^{13}$C NMR spectrum: 75 MHz, in CDCl$_3$, δ ppm [FIG. 8] 177.5(s), 151.2(s), 103.1(d), 101.9(s), 94.6(d), 85.8 (s), 80.1(d), 78.1(d), 77.6(s), 76.2(d), 75.8(d), 73.1(s), 70.2(d), 69.8(d), 68.9(d), 66.4(d), 65.8(d), 63.1(d), 52.8 (d), 49.5(q), 44.6(d), 43.5(d), 42.6(t), 34.6(t), 33.1(t), 30.9(q), 30.4(d), 26.2(q), 21.6(q), 21.4(q), 21.0(q), 20.5 (q), 20.0(q), 18.2(q), 16.7(q), 15.3(q), 13.2(q), 12.0(q), 8.6(q)

Example 3

Forty milliliters of a medium containing 1% glucose, 1% tryptone and 0.6% yeast extract (pH 7.0) placed in a 200 ml Erlenmeyer flask was inoculated with the *Saccharothrix mutabilis* subsp. *capreola* (*Nocardia capreola*) IFO 12847 strain cultivated in a yeast extract, malt extract agar slant medium, and cultivation was carried out at 28° C. for 24 hours on a rotary shaker. Then, 5 ml portions of the resulting culture solution were poured into respective test tubes, and frozen at −80° C. to store them. The portions of the culture solution were thawed at room temperature, and 1 ml portions thereof were each transferred to 40 ml portions of the above-mentioned medium placed in 200 ml Erlenmeyer flasks, followed by cultivation at 28° C. for 24 hours on a rotary shaker to obtain seed culture solutions. Then, 1 ml portions of the resulting seed culture solutions were each transferred to the above-mentioned medium placed in 200 ml Erlenmeyer flasks, and cultivated at 28° C. for 30 hours on a rotary shaker. After 24 hours of this cultivation, 1 ml of an aqueous solution of the lactobionate of the compound (1) (6 mg/ml) was added to each of the flasks.

Example 4

The culture solution (3 liters) obtained in Example 3 was centrifuged at 4° C. at 8,000 rpm for 10 minutes, and the supernatant (2.8 liters) was adjusted to pH 7.0. Then, the supernatant was subjected to Diaion HP-20 (300 ml) column chromatography, and washed with a 50% aqueous solution of methanol (1.5 liters), followed by elution with 80% methanol/0.005N hydrochloric acid (900 ml). The eluate was adjusted to pH 7.0, and methanol was removed by distillation. The resulting aqueous layer was adjusted to pH 8, and extracted three times with ethyl acetate (100 ml). The resulting ethyl acetate layers were combined and washed with water (100 ml), followed by drying with sodium sulfate. Then, the solution was concentrated and evaporated to dryness to obtain a crude powder (203 mg). The resulting crude powder (200 mg) was subjected to silica gel chromatography (10 ml), and fractions eluted with chloroform:methanol [98:2 to 95:5 (70 ml)] were collected. The resulting solution was concentrated and evaporated to dryness to obtain 111 mg of a powder containing the compound (4). Further, fractions eluted with chloroform:methanol [95:5 (50 ml)] were collected. The resulting solution was concentrated and evaporated to dryness to obtain 45 mg of a powder containing the compound (3). Furthermore, 110 mg of the powder containing the compound (4) was subjected to preparative HPLC [column; ODS, YMC-Pack, D-ODS-5, mobile phase; 55% methanol/0.02M phosphate buffer (pH 4), flow rate; 10 ml/minute], and fractions containing the compound (4) were collected. The resulting solution was adjusted to pH 7.4, followed by concentration to about 20 ml under reduced pressure. The solution was extracted with ethyl acetate at pH 8, and the ethyl acetate layer was concentrated and evaporated to dryness to obtain a purified powder of the compound (4) (43 mg).

Next, 45 mg of the powder containing the compound (3) was subjected to preparative HPLC [column; ODS, YMC-Pack, D-ODS-5, mobile phase; 28% acetonitrile/0.02M phosphate buffer (pH 4), flow rate; 10 ml/minute], and fractions containing the compound (3) were collected. The resulting solution was adjusted to pH 7.4, followed by concentration to about 5 ml under reduced pressure. The solution was extracted with ethyl acetate at pH 8, and the ethyl acetate layer was concentrated and evaporated to dryness to obtain a purified powder of the compound (3) (4.3 mg).

Example 5

Seed culture solutions of the *Amycolatopsis tolypophorus* (*Streptomyces tolypophorus*) IFO 13151 strain were prepared according to the method of Example 3. Then, 1 ml portions thereof were transferred to 40 ml portions of the medium shown in Example 3 in 200 ml Erlenmeyer flasks, and cultivated at 28° C. for 68 hours on a rotary shaker. After 48 hours of this cultivation, 1 ml of an aqueous solution of the lactobionate of the compound (1) (12 mg/ml) was added to each of the flasks.

Example 6

The culture solution (3 liters) obtained in Example 5 was centrifuged, and the supernatant (2.9 liters) was adjusted to pH 7.0. Then, the supernatant was subjected to Diaion HP-20 (300 ml) column chromatography, and washedwith a 50% aqueous solution of methanol (1.5 liters), followed by elution with 80% methanol/0.005N hydrochloric acid (900 ml). The eluate was adjusted to pH 7.0, and methanol was removed by distillation. The resulting aqueous layer (100 ml) was adjusted to pH 8, and extracted three times with ethyl acetate (100 ml). The resulting ethyl acetate layers were combined and washed with water (100 ml), followed by drying with sodium sulfate. Then, the solution was concentrated and evaporated to dryness to obtain a crude powder (415 mg). The resulting crude powder (410 mg) was subjected to silica gel chromatography (20 ml), and fractions eluted with chloroform:methanol [98:2 (120 ml)] were collected. The resulting solution was concentrated and evaporated to dryness to obtain 218 mg of a powder containing the compound (4). Further, this powder (215 mg) was subjected to preparative HPLC [column; ODS, YMC-Pack, D-ODS-5, mobile phase; 57% methanol/0.02M phosphate buffer (pH 4), flow rate; 10 ml/minute], and fractions containing the compound (4) were collected. The resulting solution was adjusted to pH 7.4, followed by concentration to about 50 ml under reduced pressure. The solution was extracted with ethyl acetate at pH 8, and the ethyl acetate layer was concentrated and evaporated to dryness to obtain a purified powder of the compound (4) (102 mg).

Example 7

Seed culture solutions of the *Dactylosporangium variesporum* (IFO 14104) strain were prepared according to the method of Example 3. Then, 1 ml portions thereof were transferred to 40 ml portions of the medium shown in Example 3 in 200 ml Erlenmeyer flasks, and cultivated at 28° C. for 24 hours on a rotary shaker to obtain seed culture solutions. Then, 1 ml portions of the resulting seed culture solutions were each transferred to the above-mentioned medium in 200 ml Erlenmeyer flasks, and cultivated at 28° C. for 48 hours on a rotary shaker. After 24 hours of this cultivation, the compound (1) (1 g/10 liters of culture solution) was added.

Example 8

The culture solution obtained in Example 7 was centrifuged, and the supernatant (9.0 liters) was adjusted to pH 7.0. Then, the supernatant was subjected to Diaion HP-20 (900 ml) column chromatography, and washed with a 50% aqueous solution of methanol (4.5 liters), followed by elution with 80% methanol/0.005N hydrochloric acid (2.7 liters). The eluate was adjusted to pH 7.0, and methanol was removed by distillation. The resulting aqueous layer (250 ml) was adjusted to pH 8, and extracted three times with ethyl acetate (250 ml). The resulting ethyl acetate layers were combined and washed with water (250 ml), followed by drying with sodium sulfate. Then, the solution was concentrated and evaporated to dryness to obtain a crude powder (896 mg). The resulting crude powder (895 mg) was subjected to silica gel chromatography (40 ml), and fractions eluted with chloroform:methanol [98:2 (240 ml)] were collected. The resulting solution was concentrated and evaporated to dryness to obtain 468 mg of a powder containing the compounds (4), (5) and (6). Further, this powder was subjected to preparative HPLC [column; ODS, YMC-Pack, D-ODS-5, mobile phase; 32% acetonitrile/0.02M phosphate buffer (pH 4), flow rate; 10 ml/minute], and fractions having an elution capacity of 190 to 240 ml (fractions containing compound (5)), fractions having an elution capacity of 240 to 285 ml (fractions containing compound (4)) and fractions having an elution capacity of 300 to 405 ml (fractions containing compound (6)) were each collected. Each of the resulting solutions was adjusted to pH 7.4, followed by concentration to about 10 ml under reduced pressure. Each of the solutions were extracted with ethyl acetate at pH 8, and the ethyl acetate layers were concentrated and evaporated to dryness to obtain a purified powder of the compound (4) (42 mg) and a purified powder of the compound (6) (49 mg). Further, the compound (5) fractions were subjected to preparative HPLC [column; ODS, YMC-Pack, D-ODS-5, mobile phase; 25% acetonitrile/0.02M phosphate buffer (pH 4), flow rate; 10 ml/minute] again, and fractions containing the compound (5) were collected. The resulting solution was adjusted to pH 7.4, followed by concentration to about 15 ml under reduced pressure. The solution was extracted with ethyl acetate at pH 8, and the ethyl acetate layer was concentrated and evaporated to dryness to obtain a purified powder of the compound (5) (46 mg).

The physicochemical properties of the compounds (5) and (6) are as follows:

Compound (5)

(1) Molecular weight: m/z 746 (MH$^+$), 602 (MH-Cladinose) (from FAB Mass Spectrum)

(2) Molecular formula: $C_{38}H_{67}NO_{13}$ (3) UV spectrum: in MeOH Absorption maximum: 207 nm ($\epsilon$7,500)

Figure 9:
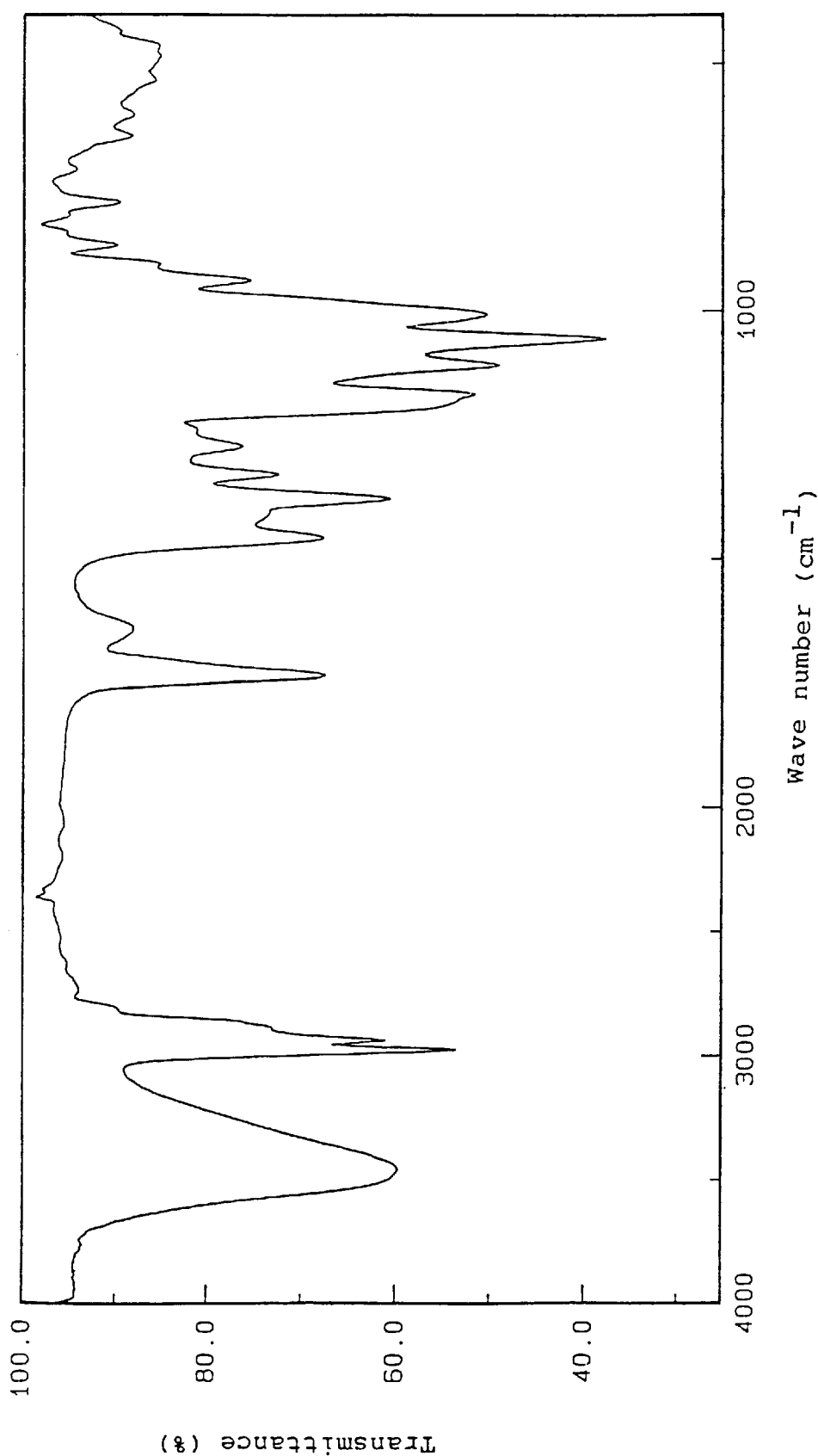
FIG. 9 shows an IR spectrum of a compound (5)

(4) IR spectrum: in a KBr tablet [FIG. 9] Main absorption peaks are shown below (wave number, cm$^{-1}$): 3460, 2970, 2940, 1730, 1640, 1460, 1380, 1330, 1270, 1170, 1110, 1060, 1010, 940

Figure 10:
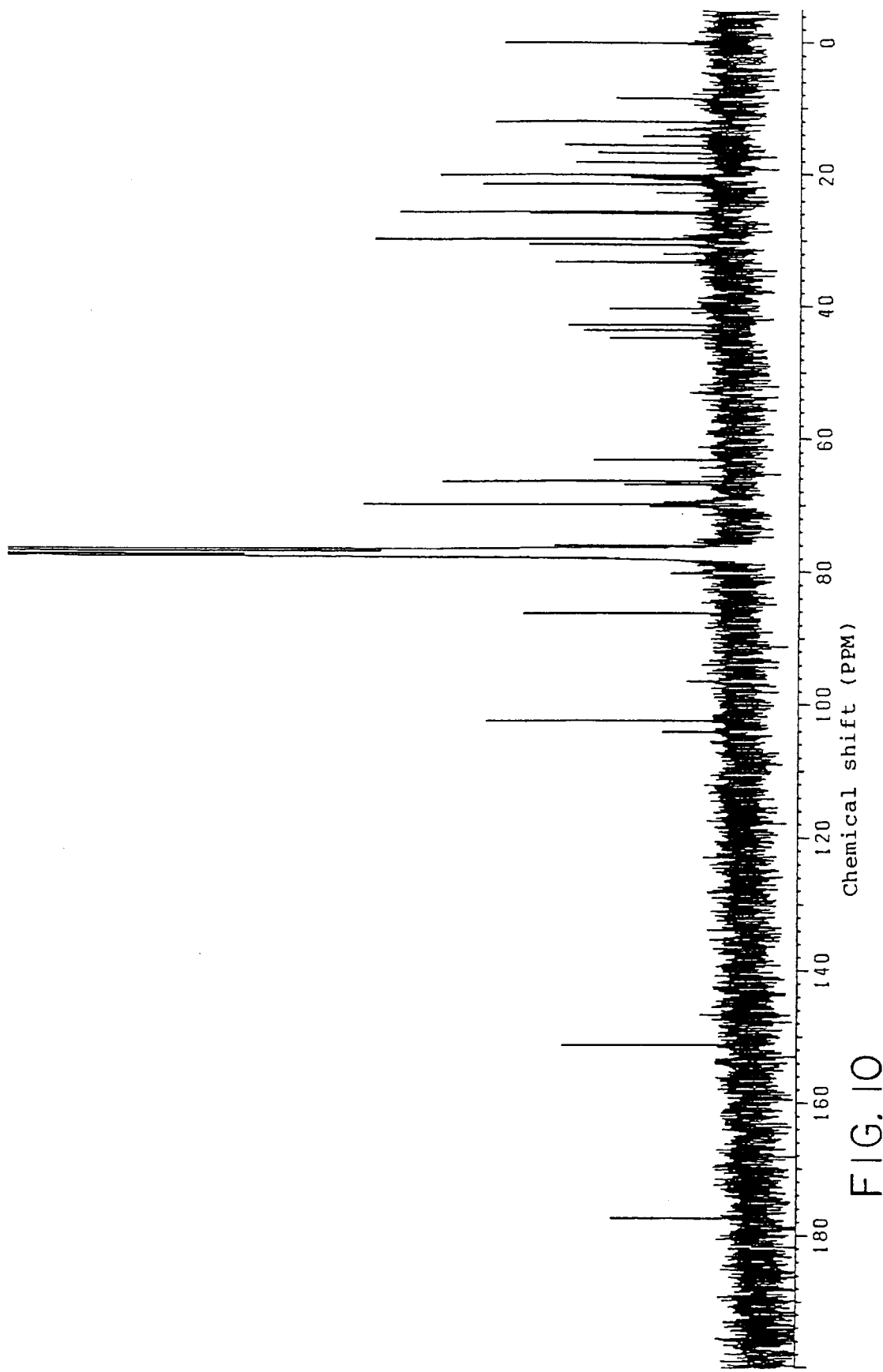
FIG. 10 shows a $^{13}C$ NMR spectrum of the compound (5)

(5) $^{13}$C NMR spectrum: 75 MHz, in CDCl$_3$ [FIG. 10] Chemical shifts are shown below ($\delta$ ppm) 177.2(s), 151.1(s), 104.0(d), 102.3(s), 96.3(d), 86.1(s), 80.1(d), 77.2(d), 76.4(d), 75.9(d), 70.1(d), 69.8(d), 69.8(s), 69.4 (d), 66.8(d), 66.3(d), 63.1(d), 53.0(d),.44.7(d),. 43.5(d), 42.8(t), 40.2(t), 33.2(t), 30.6(q), 30.5(d), 25.9(q), 25.6 (q), 21.4(q), 20.6(q), 20.4(q), 20.0(q), 18.1(q), 16.6(q), 15.5(q), 13.2(q), 12.0(q), 8.4(q)

Compound (6)

(1) Molecular weight: m/z 730 (MH$^+$), 586 (MH-Cladinose) (from FAB Mass Spectrum)

(2) Molecular formula: $C_{38}H_{67}NO_{12}$ (3) UV spectrum: in MeOH Absorption maximum: 206 nm ($\epsilon$7,400)

Figure 11:
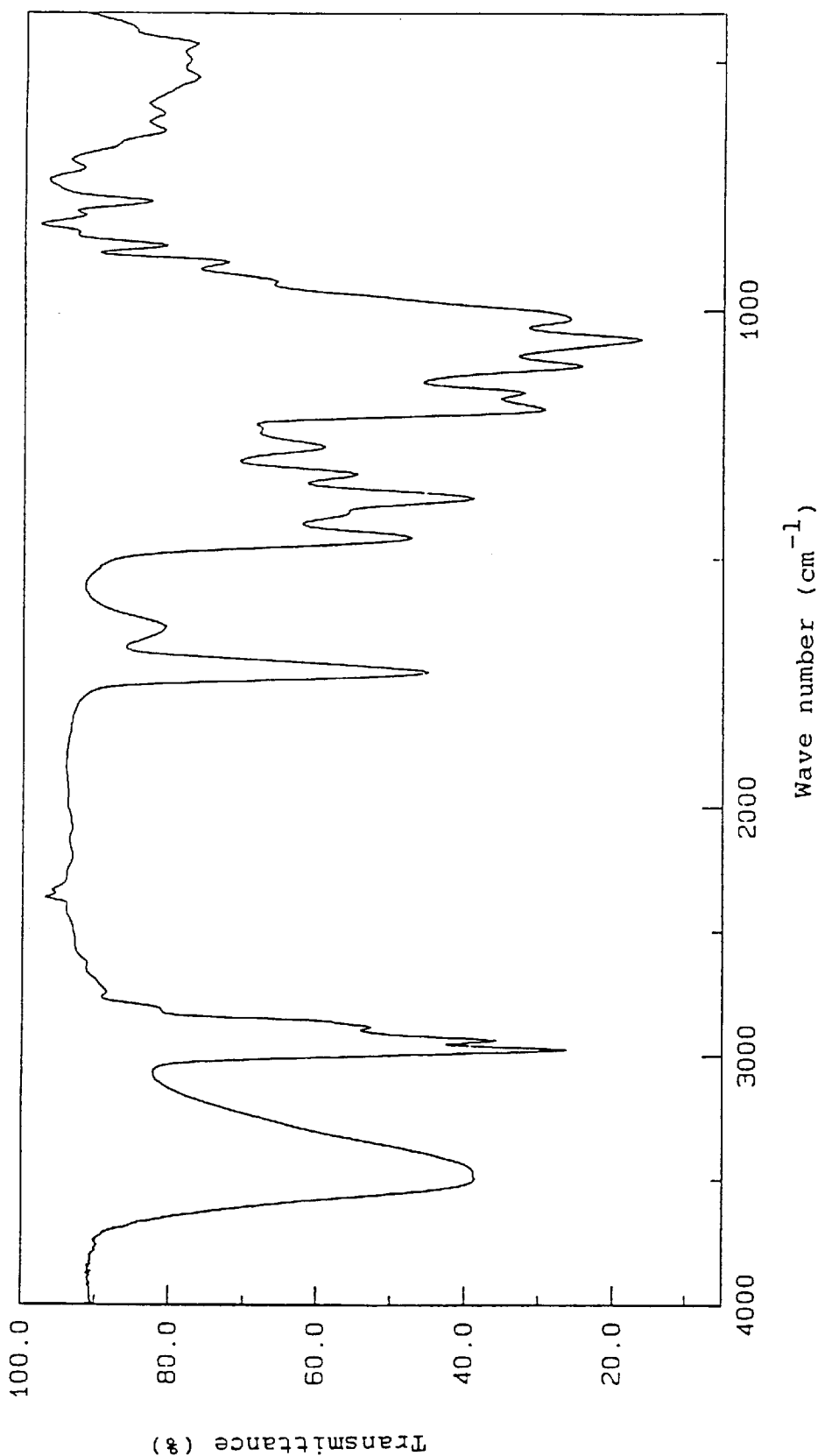
FIG. 11 shows an IR spectrum of a compound (6)

(4) IR spectrum: in a KBr tablet [FIG. 11] Main absorption peaks are shown below (wave number, cm$^{-1}$): 3490, 2970, 2940, 1730, 1640, 1460, 1380, 1330, 1270, 1200, 1160, 1110, 1060, 1020

Figure 12:
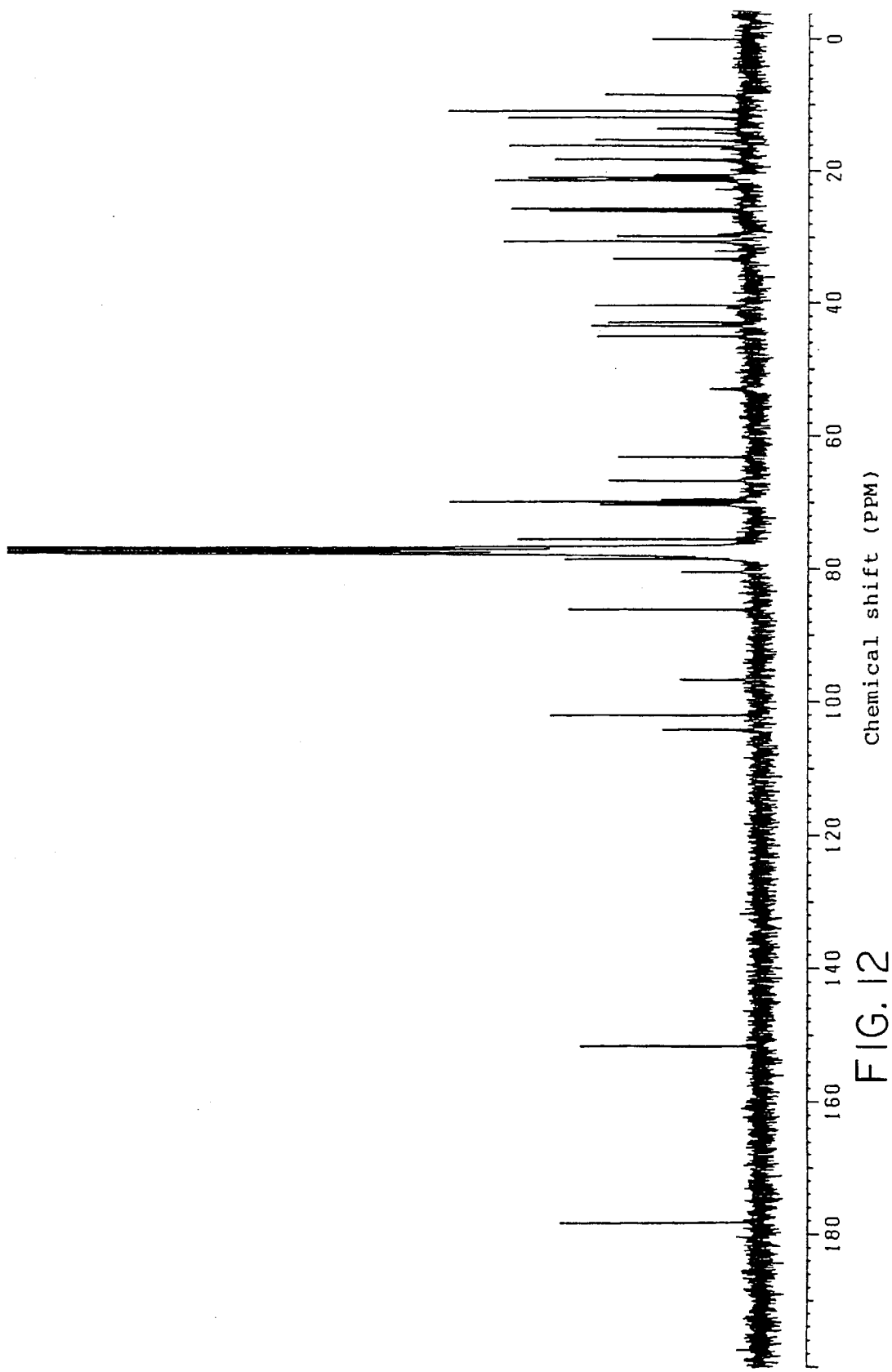
FIG. 12 shows a $^{13}C$ NMR spectrum of the compound (6)

(5) $^{13}$C NMR spectrum: 75 MHz, in CDCl$_3$ [FIG. 12] Chemical shifts are shown below ($\delta$ ppm) 178.2(s), 151.5(s), 104.1(d), 101.9(s), 96.6(d), 86.0(s), 80.4(d), 78.4(d), 77.2(d), 76.5(d), 75.4(s), 70.2(d), 70.2(d), 69.8 (s), 69.4(d), 66.7(d), 63.1(d), 52.8(d), 45.0(d), 43.3(d), 42.8(t), 40.3(t), 33.2(t), 30.6(q), 30.5(d), 26.0(q), 25.6 (q), 21.4(q), 21.0(t), 20.7(q), 20.5(q), 18.2(q), 16.1(q), 15.2(q), 13.6(q), 11.9(q), 10.9(q), 8.5(q)

Example 9

Forty milliliters of a medium containing 2% glucose, 3% soluble starch, 1% raw soybean powder, 0.3% corn steep liquor, 0.5% polypeptone, 0.3% sodium chloride and 0.5% precipitated calcium carbonate (pH 7.0) placed in a 200 ml Erlenmeyer flask was inoculated with the *Dactylosporangium variesporum* (IFO 14104) strain cultivated in a yeast extract, malt extract agar slant medium, and cultivation was carried out at 28° C. for 48 hours on a rotary shaker. Then, 5 ml portions of the resulting culture solution were poured into respective test tubes, and frozen at –80° C. to store them. The portions of the frozen culture solution were thawed at room temperature, and 5 ml thereof was transferred to 500 ml of a medium comprising 1% glucose, 1% tryptone and 0.6% yeast extract (pH 7.0) placed in a 3 liter Sakaguchi flask, followed by cultivation at 28° C. for 24 hours on a reciprocating shaker to obtain a seed culture solution. In a 200 liter stainless tank was prepared and sterilized 120 liters of a medium comprising 1% glucose, 1% tryptone and 0.6% yeast extract (pH 7.0). The medium was inoculated with 1.5 liters of the above-mentioned seed culture solution, and cultivated at an amount of aeration of 120 liters/minute at a number of stirring of 120 rpm at 28° C. for 24 hours to obtain a tank culture solution. After 24 hours of this cultivation, a 80% ethanol solution containing the compound (1) (12 g/750 ml) was added.

Example 10

A filter aid, Radiolite (3 kg, Showa Kagaku Kougyou), was added to the culture solution (112 liters) obtained in Example 9, and filtered. The resulting filtrate (108 liters) was adjusted to pH 7.0. Then, the filtrate was subjected to Diaion HP-20 (10 liters) column chromatography, and washed with a 50% aqueous solution of methanol (50 liters), followed by elution with 80% methanol/0.005N hydrochloric acid (30 liters). The eluate was adjusted to pH 7.0, and methanol was removed by distillation. The resulting aqueous layer (7 liters) was adjusted to pH 8, and extracted twice with ethyl acetate (5 liters). The resulting ethyl acetate layers were combined and washed with water (5 liters), followed by drying with sodium sulfate. Then, the solution was concentrated and evaporated to dryness to obtain a crude powder (4.3 g). The obtained crude powder was subjected to silica gel chromatography (200 ml), and fractions eluted with chloroform:methanol [98:2 (400 ml)] and fractions eluted with chloroform:methanol [98:2 (200 ml) and 95:5 (100 ml)] were each collected. The resulting solutions were concentrated and evaporated to dryness to obtain powders I (972 mg) and II (392 mg) containing the compounds (4), (5) and (6) in different amounts, respectively. The powder I was subjected to Sephadex LH-20 (500 ml, Pharmacia, Sweden) chromatography, and fractions eluted with methanol were collected. The resulting solution was concentrated and evaporated to dryness to obtain a powder I-1 (506 mg) containing the compounds (4), (5) and (6). The powder I-1 (500 mg) and the powder II (392 mg) were each subjected to preparative HPLC [column; ODS, YMC-Pack, S-363 I-15, mobile phase; 30% acetonitrile/0.02M phosphate buffer (pH 4), flow rate; 20 ml/minute], and the content of each eluted fraction was confirmed by HPLC for analysis. Fractions containing the compound (4) and fractions containing the compounds (5) and (6) were each collected, and adjusted to pH 7.4, followed by concentration. The concentrated solutions were extracted with ethyl acetate at pH 8. The ethyl acetate layers were concentrated and evaporated to dryness to obtain a purified powder of the compound (4) (104 mg) and a mixture of the compounds (5) and (6). The mixture was subjected to preparative HPLC [column; ODS, YMC-Pack, D-ODS-5, mobile phase; 25% acetonitrile/0.02M phosphate buffer (pH 4), flow rate; 10 ml/minute] again, and fractions containing the compounds (5) and (6) were collected. The resulting solution was adjusted to pH 7.4, followed by concentration. The concentrated solution was extracted with ethyl acetate at pH 8. The ethyl acetate layer was concentrated and evaporated to dryness to obtain purified powders of the compound (5) (129 mg) and the compound (6) (133 mg).

Example 11

A tank culture solution of the *Saccharothrix mutabilis* subsp. *capreola* (*Nocardia capreola*) IFO 12847 strain was prepared in a manner similar to that of Example 9. After 24 hours of this cultivation, a 80% ethanol solution of the compound (1) (16 mg/ml, 750 ml) was added, and the cultivation was continued for 6 hours. A filter aid, Radiolite (4.0 kg, Showa Kagaku Kougyou), was added to the resulting culture solution (120 liters), and filtered. The filtrate (113 liters) was adjusted to pH 7.0. Then, the filtrate was subjected to Diaion HP-20 (10 liters) column chromatography, and washed with a 50% aqueous solution of methanol (50 liters), followed by elution with 80% methanol/0.005N hydrochloric acid (30 liters). The eluate was adjusted to pH 7.5, and methanol was removed by distillation. The resulting aqueous layer (8 liters) was adjusted to pH 8, and extracted twice with ethyl acetate (5 liters). The resulting ethyl acetate layers were combined and washed with water (5 liters), followed by drying with sodium sulfate. Then, the solution was concentrated and evaporated to dryness to obtain a crude powder (6.1 g). The crude powder was subjected to silica gel chromatography (300 ml), and fractions eluted with chloroform:methanol [98:2 (900 ml) and 95:5 (200 ml)] and fractions eluted with chloroform:methanol [95:5 (600 ml)] were each collected. The resulting solutions were concentrated and evaporated to dryness to obtain powders I (2.55 g) and II (1.59 g) containing the compounds (3), (4) and (5) in different amounts, respectively. The powder I was subjected to Diaion HP-20 (100–200 meshes, 100 ml, Mitsubishi Kasei Corp.) chromatography, and eluted with 80% methanol/0.005N hydrochloric acid. The eluate was adjusted to pH 7.5, and methanol was removed by distillation. The resulting aqueous layer was adjusted to pH 8, and extracted with ethyl acetate. The resulting ethyl acetate layer was concentrated and evaporated to dryness to obtain a powder I-1 (1.58 g) containing the compounds (3), (4) and (5). Further, the powder II was subjected to Diaion HP-20 (100–200 meshes, 50 ml) chromatography, and treated in a manner similar to that of the powder I-1 to obtain a powder II-1 (722 mg) containing the compounds (3), (4) and (5). The powder I-1 (1.5 g) and the powder II-1 (720 mg) were each subjected to preparative HPLC [column; ODS, YMC-Pack, SH-36 3-15, S-15, mobile phase; 30% and 26% acetonitrile/ 0.02M phosphate buffer (pH 4), flow rate; 20 ml/minute], and the content of each eluted fraction was confirmed by HPLC for analysis. Fractions containing the compounds (3), (4) and (5) were each collected, and adjusted to pH 7.4, followed by concentration. The concentrated solutions were extracted with ethyl acetate at pH 8. The ethyl acetate layers were concentrated and evaporated to dryness to obtain a powder of the compound (3) (300 mg), a powder of the compound (4) (534 mg) and a powder of the compound (5) (323 mg). The powder of the compound (3) (300 mg) was subjected to preparative HPLC [column; ODS, YXC-Pack, D-ODS-5, mobile phase; 28% acetonitrile/0.02M phosphate buffer (pH 4), flow rate; 10 ml/minute] again, and fractions containing the compound (3) were collected. The resulting solution was adjusted to pH 7.4, followed by concentration. The concentrated solution was extracted with ethyl acetate at pH 8. The ethyl acetate layer was concentrated and evaporated to dryness to obtain a purified powder of the compound (3) (105 mg). Further, the powder of the compound (4) (534 mg) was subjected to preparative HPLC [column; ODS, YMC-Pack, SH-363-15, S-15, mobile phase; 55% methanol/ 0.02M phosphate buffer (pH 4), flow rate; 15 ml/minute] again, and fractions containing the compound (4) were collected. The resulting solution was adjusted to pH 7.4, followed by concentration. The concentrated solution was extracted with ethyl acetate at pH 8. The ethyl acetate layer was concentrated and evaporated to dryness to obtain a purified powder of the compound (4) (338 mg). Furthermore, the powder of the compound (5) (323 mg) was subjected to preparative HPLC [column; ODS, YMC-Pack, SH-363-15, S-15, mobile phase; 54% methanol/0.02M phosphate buffer (pH 4), flow rate; 15 ml/minute] again, and fractions containing the compound (5) were collected. The resulting solution was adjusted to pH 7.4, followed by concentration. The concentrated solution was extracted with ethyl acetate at pH 8. The ethyl acetate layer was concentrated and evaporated to dryness to obtain a purified powder of the compound (5) (76 mg).

Example 12

A tank culture solution of the *Saccharothrix mutabilis* subsp. *capreola* (*Nocardia capreola*) IFO 12847 strain was prepared in a manner similar to that of Example 9. After 24 hours of this cultivation, a 80% ethanol solution of the compound (2) (16 mg/ml, 750 ml) was added, and the cultivation was continued for 6 hours. A filter aid, Radiolite (3.0 kg, Showa Kagaku Kogyo), was added to the resulting culture solution (116 liters), and filtered. The filtrate (110 liters) was adjusted to pH 7.0. Then, the filtrate was subjected to Diaion HP-20 (10 liters) column chromatography, and washed with a 50% aqueous solution of methanol (50 liters), followed by elution with 80% methanol/0.005N hydrochloric acid (30 liters). The eluate was adjusted to pH 7.5, and methanol was removed by distillation. The resulting aqueous layer (10.5 liters) was adjusted to pH 8, and extracted twice with ethyl acetate (5 liters). The resulting ethyl acetate layers were combined and washed with water (5 liters), followed by drying with sodium sulfate. Then, the solution was concentrated and evaporated to dryness to obtain a crude powder (9.0 g). The crude powder was subjected to silica gel chromatography (400 ml), and fractions eluted with chloroform:methanol [98:2 (1.6 liters)] and fractions eluted with chloroform:methanol [95:5 (1.2 liters)] were each collected. The resulting solutions were concentrated and evaporated to dryness to obtain a powder I (2.9 g) containing the compound (8) and a powder II (1.68 g) containing the compounds (7) and (9). The powder II was subjected to preparative HPLC [column; ODS, YMC-Pack, SH-363-15, S-15, mobile phase; 26% acetonitrile/0.02M phosphate buffer (pH 4), flow rate; 20 ml/minute], and the content of each eluted fraction was confirmed by HPLC for analysis. Fractions containing the compounds (7) and (9) were each collected, and the resulting solutions were adjusted to pH 7.4, followed by concentration. The concentrated solutions were extracted with ethyl acetate at pH 8. The ethyl acetate layers were concentrated and evaporated to dryness to obtain a powder of the compound (7) (80 mg) and a powder of the compound (9) (783 mg). The powder of the compound (7) (80 mg) was subjected to preparative HPLC [column; ODS, YMC-Pack, D-ODS-5, mobile phase; 25% acetonitrile/0.02M phosphate buffer (pH 4), flow rate; 10 ml/minute] again, and fractions containing the compound (7) were collected. The resulting solution was adjusted to pH 7.4, followed by concentration. The concentrated solution was extracted with ethyl acetate at pH 8. The ethyl acetate layer was concentrated and evaporated to dryness to obtain a purified powder of the compound (7) (15 mg). Further, the powder of the compound (9) (783 mg) was subjected to preparative HPLC [column; ODS, YMC-Pack, SH-363-15, S-15, mobile phase; 52% methanol/0.02M phosphate buffer (pH 4), flow rate; 15 ml/minute] again, and treated in a similar manner with the above method to obtain a purified powder of the compound (9) (200 mg). Furthermore, the powder (2.9 g) containing the compound (8) was dissolved in methanol (10 ml). Then, ether (10 ml) was added thereto, and the resulting solution was concentrated to obtain crystals of the compound (8) (812 mg).

The physicochemical properties of the compound (9) are as follows:

Compound (9)

(1) Molecular weight: m/z 732 (MH$^+$), 588 (MH-Cladinose) (from FAB Mass Spectrum)

(2) Molecular formula: $C_{37}H_{65}NO_{13}$ (3) UV spectrum: in MeOH Absorption maximum: 208 nm ($\epsilon$7,100)

Figure 13:
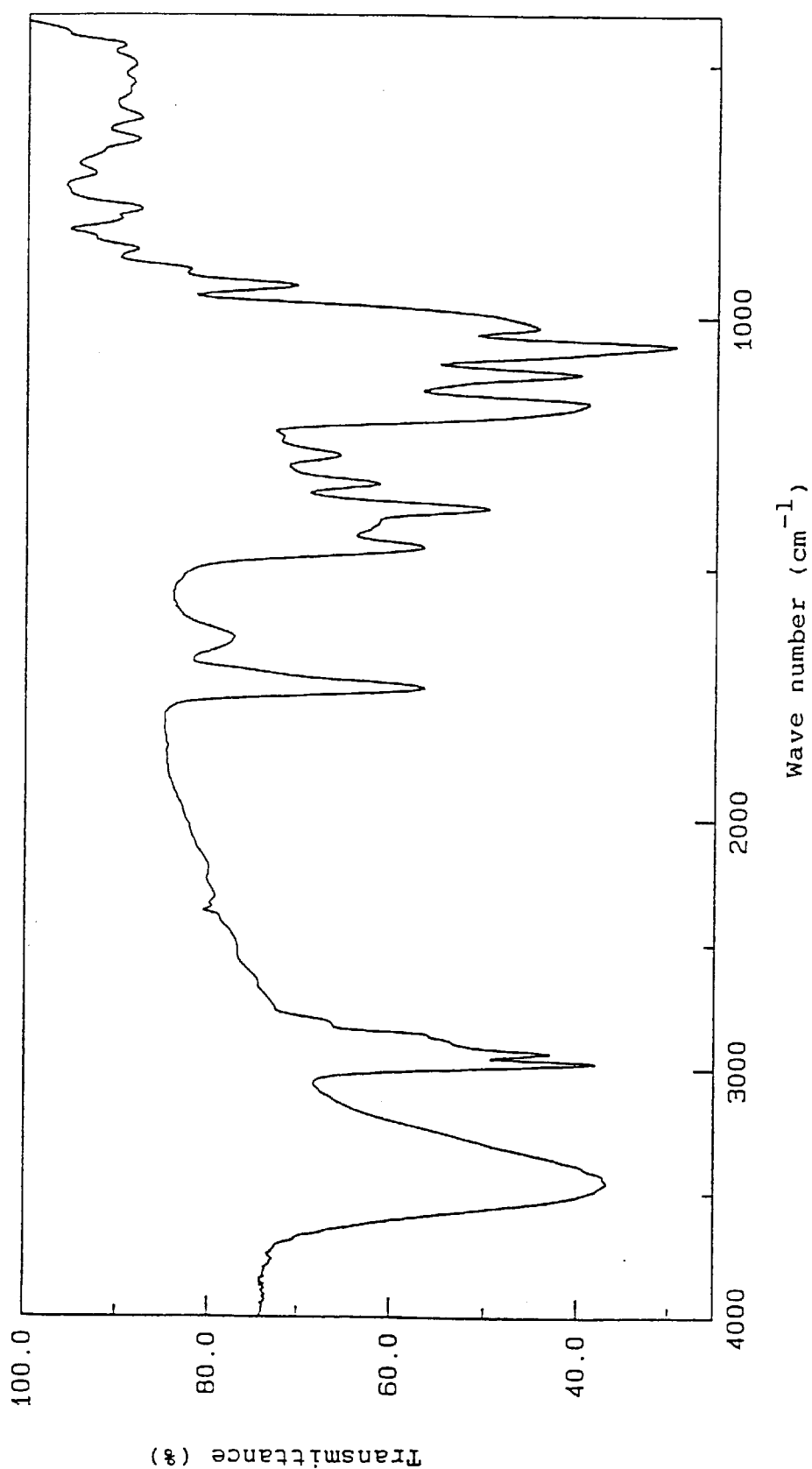
FIG. 13 shows an IR spectrum of a compound (9)

(4) IR spectrum: in a KBr tablet [FIG. 13] Main absorption peaks are shown below (wave number, cm$^{-1}$): 3455, 2975, 2935, 1735, 1635, 1455, 1375, 1330, 1275, 1170, 1115, 1055, 1020, 935

(5) $^{13}$C NMR spectrum: 75 MHz, in CDCl$_3$ [FIG. 14] Chemical shifts are shown below ($\delta$ ppm) 177.2(s), 151.2(s), 104.0(d), 102.2(s), 96.2(d), 86.1(s), 79.9(d), 77.2(s), 76.8(d), 76.3(d), 76.0(d), 70.3(d), 69.8(s), 69.8(d), 69.6(d), 66.9(d), 66.4(d), 65.0(d), 47.5(t), 44.6(d), 43.6(d), 42.7(t), 40.2(t), 36.2(q), 30.6(d), 29.5(t), 25.9(q), 25.6(q), 21.4(q), 19.9(q), 18.1(q), 16.8(q), 15.6(q), 13.9(q), 13.0(q), 12.0(q), 8.4(q)

Experimental Example 1

Effect (GMS activity) on Gastric Motor of Dogs was studied.

[Method]

Beagles having a body weigh of about 10 kg were subjected to laparotomy under pentobarbital anesthesia, and a strain gauge force transducer was attached to the gastric antrum of each of the beagles. The beagles were used for the experiment more than 2 weeks after the operation. A lead wire of the strain gauge force transducer was connected to a recorder through an amplifier and the recorder records gastric contractions. Signals from the amplifier were supplied to a signal processor (NEC Sanei).

Each of the test compounds was dissolved in ethanol, and lactobionic acid (1 mg/mg of test compound) was added thereto, followed by dilution with physiological saline. The resulting solution was intravenously given 15 minutes after termination of the natural interdigestive migrating contractions.

The area of gastric contractions induced by administration of the test compounds was measured by use of the signal processor. Taking the area at the time that the maximum contraction of the interdigestive migrating contractions was kept for 1 minute as 100%, the dosage inducing a contraction area of 200% (ED$_{200}$ value) was determined from dosage action curves.

[Results]

The ED$_{200}$ values of the respective test compounds are shown in Table 3.

TABLE 3

Results of Test Compounds on Gastric Motor of Dogs

| Compound No. | ED$_{200}$ ($\mu$g/kg, i.v.) |
| --- | --- |
| (2) | 8.0 |
| (7) | 3.2 |
| (8) | 1.8 |
| (1) | 0.9 |
| (3) | 0.5 |
| (4) | 0.4 |

As is apparent from Table 3, the active compounds (3),(4),(7) and (8) obtained by the method of the present invention exhibit a stronger GMS activity than the respective starting compounds (1) and (2).

Experimental Example 2

The action (GMS activity) of the above-mentioned compounds on the gastric motor of the dogs was measured.

[Method]

The measurement was carried out in a manner similar to that of Experimental Example 1.

[Results]

ED$_{200}$ values of the tested compounds (1),(5) and (6) are shown in Table 4.

TABLE 4

| Compound No. | ED$_{200}$ ($\mu$g/kg) |
| --- | --- |
| (5) | 0.21 |
| (6) | 0.26 |
| (1) | 0.9 |

As is apparent from Table 4, the compounds (5) and (6) obtained by the method of the present invention exhibit a stronger GMS activity than the starting compound (1).

Reference Example 1

Method for Preparing N-Demethyl-N-Isopropyl-8,9-Anhydroerythromycin B 6,9-Hemiacetal N-Demethyl-erythromycin B, a starting compound, was synthesized by a method described in Japanese Patent Unexamined Publication No.47-4232 (Abbott Laboratories, U.S.A.).

N-Demethyl-erythromycin B (4.95 g, 7.03 mmol) was dissolved in acetonitrile (25 ml), and isopropyl iodide (23.9 g, 140.6 mmol, 20 eq.) and triethylamine (35.6 g, 35.2 mmol, 5 eq.) were added thereto, followed by stirring at 55° C. for 17 hours. The solvent was removed by distillation under reduced pressure. Water (50 ml) and ethyl acetate (50 ml) were added to the residue to distribute it, and an ethyl acetate layer was separated. The aqueous layer was extracted with 30 ml of ethyl acetate. The resulting organic layers were combined, and washed twice with saturated saline (30 ml), followed by drying with anhydrous magnesium sulfate. Then, the solution was concentrated and evaporated to dryness to obtain crude N-demethyl-N-isopropylerythromycin B (6.3 g) as a pale yellow solid. This product was dissolved in acetic acid (10 ml), followed by stirring at room temperature for 1 hours. Ice (40 g) and 25% aqueous ammonia (20 ml) were added, followed by extraction with ethyl acetate (50 ml). The ethyl acetate layer was washed with saturated saline (20 ml), and then, concentrated and evaporated to dryness under reduced pressure to obtain a residue (4.86 g). This residue was subjected to silica gel chromatography (400 g, dichloromethane:methanol=10:1) to purify it. Upon crystallization from isopropyl ether-hexane, N-demethyl-N-isopropyl-8,9-anhydroerythromycin B 6,9-hemiacetal (3.20 g) was obtained as pale yellow crystals. The resulting compound can be used as a starting compound of the present invention.

The physicochemical properties of the compound are as follows:

(1) Elemental analysis $C_{39}H_{69}NO_{11} \cdot H_2O$ (745.99) Calcd. C 62.79, H 9.59, N 1.88 Found C 62.54, H 9.48, N 1.89

(2) $^{13}$C NMR spectrum: 75 MHz, in CDCl$_3$, $\delta$ ppm 178.5(s), 151.5(s), 103.0(d), 101.6(s), 94.6(d), 85.8(s), 80.2(d), 78.2(d), 77.4(d), 76.9(d), 73.1(s), 71.2(d), 70.3(d), 68.9(s), 65.6(d), 63.1(d), 52.7(d), 49.5(q), 44.6(d), 43.7(d), 43.2(d), 42.5(t), 34.7(t), 33.7(d), 33.1(s), 30.9(q), 26.3(q), 25.0(t), 21.6(q), 21.4(q), 21.1(q), 20.6(q), 18.2(q), 14.9(q), 13.1(q), 12.1(q), 10.4(q), 8.7(q), 8.7(q)

Reference Example 2

Method for Preparing 4'-Deoxy-N-Demethyl-N-Ethyl-8,9-Anhydroerythromycin A 6,9-Hemiacetal 2'-O-Acetyl-N-demethyl-N-ethyl-erythromycin A (1.31 g) was dissolved in tetrahydrofuran (44 ml), and imidazole (113 mg) and 1,1'-thiocarbonyldiimidazole (1.97 g) were added thereto, followed by reflux for 2 hours. The reaction solution was diluted with ether (100 ml), and washed twice with 5% aqueous sodium hydrogencarbonate, and with water (50 ml) and saturated saline (50 ml), followed by drying with anhydrous sodium sulfate. Then, the solution was concentrated and evaporated to dryness under reduced pressure to obtain a crude extract (1.85 g). This extract was subjected to silica gel chromatography (110 ml). When the eluted fractions of acetone/toluene (2:8) were concentrated, 2'-O-acetyl-4"-O-imidazothiocarbonyl-N-demethyl-N-ethyl-erythromycin A (1.10 g, yield: 74%) was obtained. The physicochemical properties of the compound are as follow:

(1) $^1$H NMR spectrum(300 MHz, in CDCl$_3$): δ ppm, 8.25, 7.56, 7.03 (imidazole), 5.47 (4"-H)

(2) $^{13}$C NMR spectrum: 75 MHz, in CDCl$_{31}$ $_{\delta\ ppm}$ 184.4 (s), 175.3(s), 169.9(s), 136.7(d), 131.0(d), 117.8(d), 100.7(d), 95.9(d), 86.9(d), 83.7(d), 80.0(d), 76.8(d), 74.8(s), 74.5(s), 73.2(s), 71.4(d), 69.0(d), 68.1(d), 63.3 (d), 62.6(d), 49.4(q), 47.8(t), 45.2(d), 44.6(d), 38.7(d), 37.9(t), 37.7(d), 36.7(q), 35.4(t), 31.0(t), 26.9(q), 21.3 (q), 21.3(q), 21.1(q), 21.1(t), 18.1(q), 18.1(q), 16.3(q), 16.0(q), 14.0(q), 12.0(q), 10.6(q), 9.0(q)

2'-O-Acetyl-4"-O-imidazothiocarbonyl-N-demethyl-N-ethyl-erythromycin A (380 mg) thus obtained was dissolved in toluene (30 ml), and 2,2'-azodiisobutyronitrile (14 mg) and tributyltin hydride (0.176 ml) were added thereto, followed by reflux for 3 hours. The reaction solution was concentrated and evaporated to dryness, and the residue was distributed with hexane (50 ml)-acetonitrile (50 ml). After concentration, the lower layer was subjected to silica gel chromatography (20 ml). When the eluted fractions of acetone/toluene (15:85) were concentrated, 2'-O-acetyl-4'-deoxy-N-demethyl-N-ethyl-erythromycin A (185 mg, yield: 56%) was obtained.

The whole amount of this compound was dissolved in methanol (6.0 ml), and potassium carbonate (16 mg) was added thereto, followed by stirring at room temperature for 24 hours. The reaction solution was concentrated and evaporated to dryness, and diluted with ethyl acetate (15 ml). Then, the resulting solution was washed with saturated aqueous sodium hydrogencarbonate (10 ml) and saturated saline (10 ml), followed by drying with anhydrous sodium sulfate. Then, the solution was concentrated and evaporated to dryness under reduced pressure. The resulting product was stirred in acetic acid/dichloromethane (1:3, 4.0 ml) at room temperature for 2 hours. The reaction solution was poured on saturated aqueous sodium hydrogencarbonate (15 ml) under ice cooling, and the aqueous layer was extracted twice with chloroform (15 ml). The organic layer was washed with 5% aqueous sodium hydrogencarbonate (15 ml) and 15% saline (15 ml), followed by drying with anhydrous sodium sulfate. Then, the solution was concentrated and evaporated to dryness under reduced pressure. The residue was dissolved in methanol, and subjected to reversed phase preparative HPLC (column; ODS, YMC-Pack, D-ODS-5, mobile phase; 38% acetonitrile/0.02M phosphate buffer, pH 4). Fractions having an elution capacity of 300 to 470 ml were concentrated. Ethyl acetate (15 ml) and saturated aqueous sodium hydrogencarbonate (15 ml) were added to the concentrate to partition it. The aqueous layer was extracted with ethyl acetate (10 ml). The resulting organic layers were combined and washed with saturated aqueous sodium hydrogencarbonate (10 ml) and saturated saline (10 ml), followed by drying with anhydrous sodium sulfate. Then, the solution was concentrated and evaporated to dryness under reduced pressure. As a result, 4"-deoxy-N-demethyl-N-ethyl-8,9-anhydroerythromycin A 6,9-hemiacetal (12 mg) was obtained. The resulting compound can be used as a starting compound of the present invention. The physicochemical properties of the compound are as follows:

(1) HPLC analysis: ODS, 37% acetonitrile/0.02M phosphate buffer, retention time; 18.8 minutes, control compound (2); 7.9 minutes (2) $^{13}$C NMR spectrum: 75 MHz, in CDCl$_3$, δ ppm 178.6(s), 151.8(s), 102.6(d), 101.6(d), 95.3(d), 85.5(s), 79.8(d), 78.3(d), 76.1(d), 75.4(s), 70.5(s), 70.5(d), 69.6 (d), 68.4(s), 64.8(d), 61.8(d), 49.4(q), 47.7(t), 46.0(t), 44.7(d), 43.4(d), 42.5(t), 36.2(q), 33.4(t), 30.5(d), 29.6 (t), 26.4(q), 25.7(q), 21.5(q), 21.3(q), 21.1(t), 16.6(q), 15.1(q), 13.8(q), 13.3(q), 12.0(q), 11.0(q), 8.7(q)

(3) Molecular weight: 714(M$^+$H), 572 (M$^+$H-deoxycladinose) (from FAB mass spectrum)

The 6,9-hemiacetal-erythromycin derivatives or the salts thereof of the present invention have an excellent digestive function promoting effect and is low in toxicity, so that they are useful as the gastrointestinal function promoting agents.

What is claimed is:

1. A 6,9-hemiacetal-erythromycin compound having a hydroxyl group at the 15-position or a salt thereof.

2. The 6,9 hemiacetal-erythromycin compound or the salt thereof according to claim 1, wherein said 6,9-hemiacetal-erythromycin compound is represented by the formula (1):

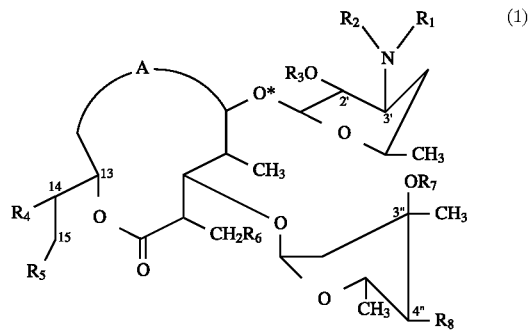

wherein $R_1$ represents hydrogen or a substituted or unsubstituted aliphatic hydrocarbon group having not more than 12 carbon atoms, selected from the group consisting of lower alkyl, cycloalkyl, lower alkenyl and lower alkynyl, and $R_2$ represents hydrogen or a substituted or unsubstituted aliphatic hydrocarbon group as defined in $R_1$, above, or $R_1$ and $R_2$ form a heterocyclic group together with the adjacent nitrogen atom; $R_3$ represents hydrogen or a substituted or unsubstituted acyl group; $R_4$ is hydrogen; $R_5$ is a hydroxyl group; $R_6$ represents hydrogen or a hydroxyl group; $R_7$ represents hydrogen or a methyl group;

$R_8$ is selected from the group consisting of hydrogen, a hydroxyl group, a substituted or unsubstituted acyloxy group, and a substituted or unsubstituted alkoxy group; and —A— represents the formula (2):

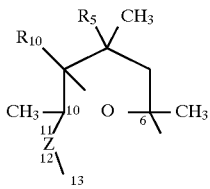

wherein $R_9$ and $R_{10}$ both represent hydrogen or together form a double bond;
and Z is selected from the group consisting of (i) the formula (3):

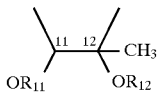

wherein $R_{11}$ is selected from the group consisting of hydrogen, a substituted or unsubstituted acyl group, and a substituted or unsubstituted alkyl group; and $R_{12}$ is selected from the group consisting of hydrogen, a lower carboxylacyl group, and an alkyl group which is unsubstituted or substituted by an alklthio group, (ii) the formula (4):

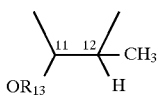

wherein $R_{13}$ is the same as defined in $R_{11}$ above, (iii) the formula (5):

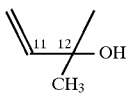

(iv) the formula (6):

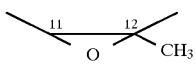

and (v) the formula (7):

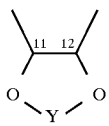

wherein Y is selected from the group consisting of
(a) the formula >B—$R_{14}$; wherein $R_{14}$ represents an alkyl group or an aryl group,
(b) >S=O, >C=O, >C=S, and
(c) the formula (8):

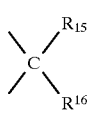

wherein $R_{15}$ and $R_{16}$, which may be the same or different, are selected from the group consisting of hydrogen and alkyl groups, or from a cyclic alkyl group together with the adjacent carbon atom, or one of them is selected from the group consisting of hydrogen, an alkyl group, and an aryl group, and the other represents a dialkylamino group, or -A- represents the formula (9):

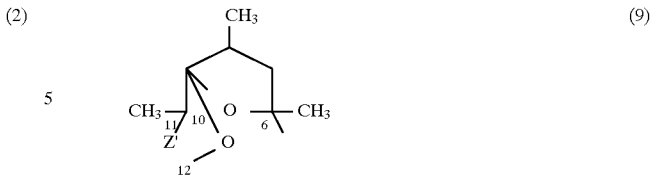

wherein Z' represents the formula (10):

wherein $R_{17}$ is selected from the group consisting of hydrogen, a substituted or unsubstituted acyl group, and a substituted or unsubstituted alkyl group.

3. The 6,9-hemiacetal-erythromycin compound or the salt thereof according to claim 1, wherein said 6,9-hemiacetal-erythromycin compound is represented by the formula (ii):

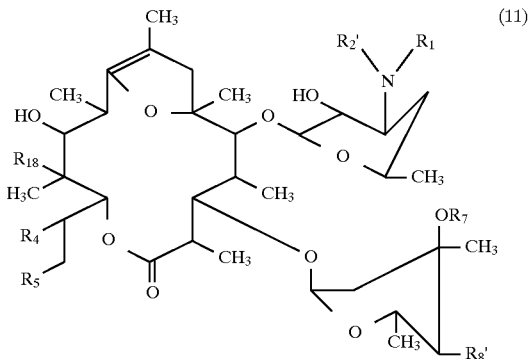

wherein $R_1$ represents hydrogen or a substituted or unsubstituted aliphatic hydrocarbon group having not more than 12 carbon atoms and being selected from the group consisting of lower alkyl, cycloalkyl, lower alkenyl and lower alkynyl; $R_2$, represents a substituted or unsubstituted aliphatic hydrocarbon group as defined in $R_1$ above; and $R_4$ is hydrogen $R_5$ is a hydroxyl group; $R_7$ represents hydrogen or a methyl group; $R_8$, represents hydrogen or a hydroxyl group; and $R_8$, represents hydrogen or a hydroxyl group.

4. The 6,9-hemiacetal-erythromycin compound or the salt thereof according to claim 3, wherein said 6,9-hemiacetal-erythromycin compound is represented by the formula (12):

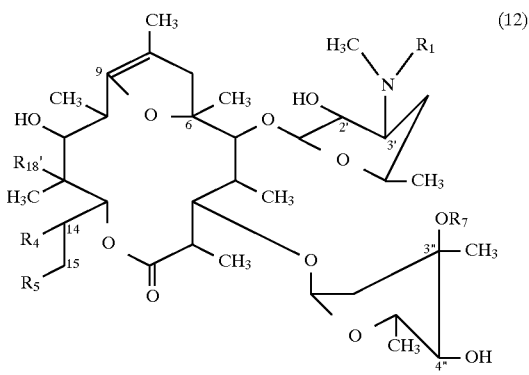

wherein $R_1$ represents hydrogen or a substituted or unsubstituted aliphatic hydrocarbon group having not more than 12 carbon atoms, selected from the group consisting of lower alkyl, cycloalkyl, lower alkenyl and lower alkynyl; $R_4$ is a hydrogen; $R_5$ is a hydroxyl group; $R_7$ represents hydrogen or a methyl group, wherein $R_{18}$, represents hydrogen where $R_7$ is methyl.

5. The 6,9-hemiacetal-erythromycin compound or the salt thereof according to claim 2, wherein said 6,9-hemiacetal-erythromycin compound is represented by the formula (13):

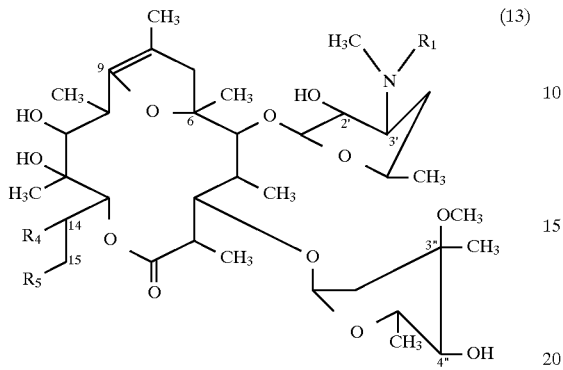
(13)

wherein $R_1$ represents hydrogen or a substituted or unsubstituted aliphatic hydrocarbon group having not more than 12 carbon atoms selected from the group consisting of lower alkyl, cycloalkyl, lower alkeny and lower alkynyl, $R_4$ is hydrogen; $R_5$ is a hydroxyl group.

6. The 6,9-hemiacetal-erythromycin compound or the salt thereof according to claim 3, in which $R_1$ and $R_2$ may be the same or different and represent a substituted or unsubstituted cycloalkyl group.

7. The 6,9-hemiacetal-erythromycin compound or the salt thereof according to claim 2, in which $R_1$ and $R_2$ may be the same or different and represent a substituted or unsubstituted $C_{1-6}$ alkyl group.

8. The 6,9-hemiacetal-erythromycin compound or the salt thereof according to claims 4 or 5 in which $R_1$ is an isopropyl or an ethyl group.

9. The 6,9-hemiacetal erythromycin compound or the salt thereof according to claim 2, wherein —A— represents the formula (2).

10. The 6,9-hemiacetal-erythromycin compound of the salt thereof according to claim 4, wherein $R_1$ is isopropyl, $R_{18}$, is OH, and $R_7$ is methyl.

11. The 6,9-hemiacetal-erythromycin compound of the salt thereof according to claim 4, wherein $R_1$ is ethyl, $R_{18}$, is OH, and $R_7$ is methyl.

12. A gastrointestinal function promoting agent comprising the 6,9-hemiacetal-erythromycin compound or the salt thereof according to claim 1 and a pharmaceutically acceptable carrier or diluent.

13. A gastrointestinal function promoting agent comprising the 6,9-hemiacetal-erythromycin compound or the salt thereof according to claim 2 and a pharmaceutically acceptable carrier or diluent.

14. A gastrointestinal function promoting agent comprising the 6,9-hemiacetal-erythromycin compound of the salt thereof according to claim 3 and a pharmaceutically acceptable carrier or diluent.

15. A process for preparing a 6-9-hemiacetal-erythromycin compound having a hydroxyl group at the 15-position or a salt thereof, which comprises reacting a 6,9-hemiacetal-erythromycin compound or a salt thereof with an oxidase derived from an actinomycete or from a liver of a mammal.

16. The process for preparing the 6,9-hemiacetal-erythromycin compound represented by the formula (1):

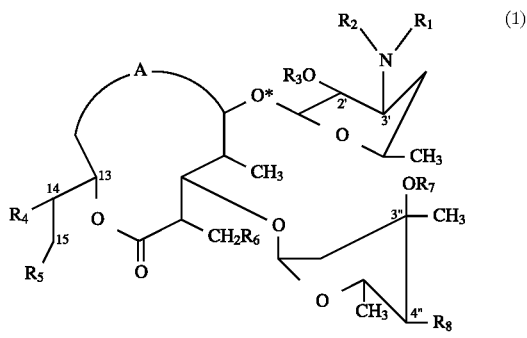
(1)

wherein symbols have the same meaning as defined in claim 1 or 2,. or the salt thereof, which, comprises reacting a 6,9-hemiacetal-erythromycin compound represented by the formula (14):

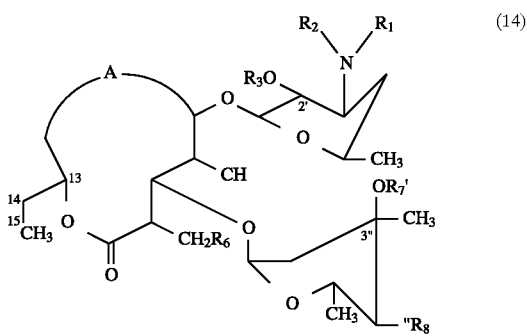
(14)

wherein $R_7$ represents hydrogen or a methyl group, and the other symbols have the same meanings as defined in claim 2 or a salt thereof with an oxidase derived from an actinomycete or a liver of a mammal.

17. The process for preparing the 6,9-hemiacetal-erythromycin compound represented by the formula (11):

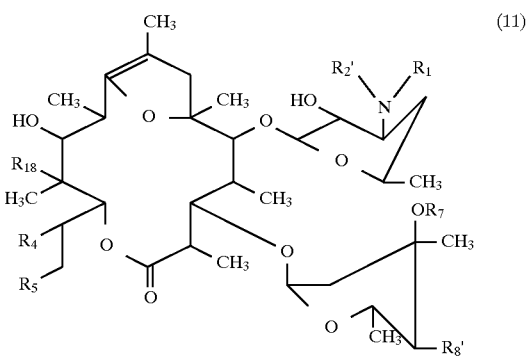
(11)

wherein the symbols have the same meanings as defined in claim 3 or the salt thereof, which comprises reacting a 6,9-hemiacetal-erythromycin compound represented by the formula (15):

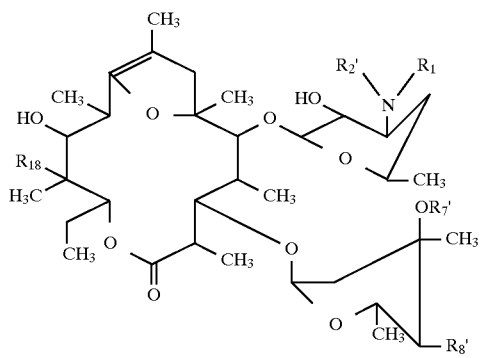
(11)

wherein $R_1$, $R_2$, $R_8$ and $R_{18}$ have the same meanings as defined in claim 3 and $R_7$ represents hydrogen or a methyl group, or a salt thereof with an oxidase derived from an actinomycete or a liver of a mammal.

18. A process for preparing the 6,9-hemiacetal-erythromycin compound represented by the formula (16):

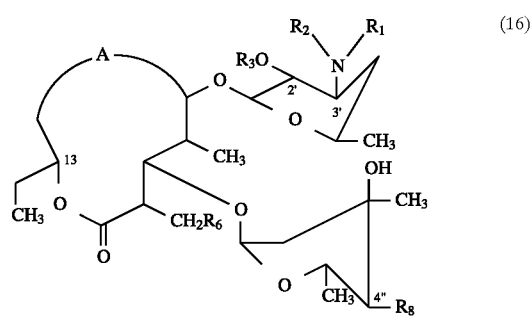
(16)

wherein $R_3$ represents hydrogen or a substituted or unsubstituted aliphatic hydrocarbon group and $R_2$ represents hydrogen or a substituted or unsubstituted aliphatic hydrocarbon group, or $R_1$ and $R_2$ form a heterocyclic group together with the adjacent nitrogen atom; $R_3$ represents hydrogen or a substituted or unsubstituted acyl group; $R_6$ represents hydrogen or a hydroxyl group; $R_8$ represents hydrogen, a hydroxyl group, a substituted or unsubstituted acyloxy group or a substituted or unsubstituted alkoxy group;

and —A— represents the formula (2):

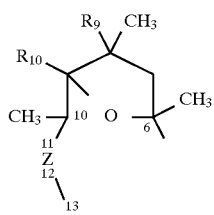
(2)

wherein $R_9$ and $R_{10}$ both represent hydrogen or both form a chemical bond;
and Z represents the formula (3):

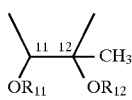
(3)

wherein $R_{11}$ represents hydrogen, a substituted or unsubstituted acyl group or a substituted or unsubstituted alkyl group; and $R_{12}$ represents hydrogen, a lower carboxylacyl group or an alkyl group which may have alkylthio as a substituent, or Z represents the formula (4):

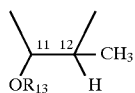
(4)

wherein $R_{13}$ represents hydrogen, a substituted or unsubstituted acyl group or a substituted or unsubstituted alkyl group, or Z represents the formula (5):

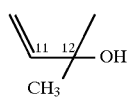
(5)

or Z represents the formula (6):

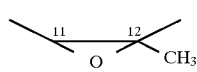
(6)

or Z represents the formula (7):

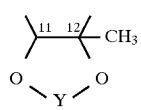
(7)

wherein Y represents the formula >B—$R_{14}$; wherein $R_{14}$ represents an alkyl group or an aryl group; >S=O, >C=O, >C=S or the formula (8):

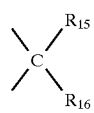
(8)

wherein $R_{15}$ and $R_{16}$, which may be the same or different, represent hydrogen or alkyl groups or form a cyclic alkyl group together with the adjacent carbon atom, or one of them represents hydrogen, an alkyl group or an aryl group, and the other represents a dialkylamino group, or —A— represents the formula (9):

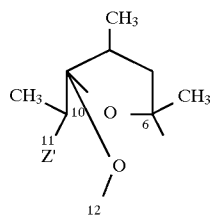
(9)

wherein Z' represents the formula (10):

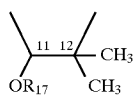
(10)

wherein $R_{17}$ represents hydrogen, a substituted or unsubstituted acyl group or a substituted or unsubstituted alkyl group, or the salt thereof, which comprises reacting a 6,9-hemiacetal-erythromycin compound represented by the formula (17):

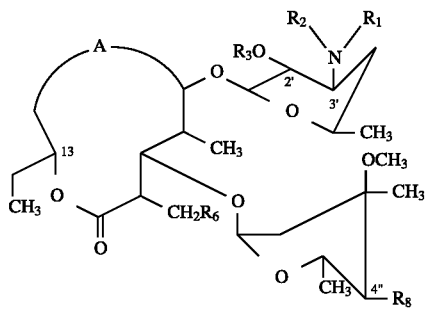
(17)

wherein $R_1$, $R_2$, $R_3$, $R_6$, $R_8$ and —A— have the same meanings as defined above, or a salt thereof with an oxidase derived from an actinomycete or a liver of a mammal.

19. A process for preparing a salt of the 6,9-hemiacetal-erythromycin compound having a hydroxyl group at the 15-position of claims 1, 2, or 3 which comprises subjecting said 6,9-hemiacetal-erythromycin compound to a quaternary ammoniating reaction.

20. The process according to claims 15, 16, 17 or 18, in which the oxidase is an oxidase derived from the liver of a dog.

21. The process according to claims 15, 16, 17 or 18, in which the oxidase is an oxidase derived from an actinomycete.

22. A process for preparing the 6,9-hemiacetal-erythromycin compound represented by the formula (18):

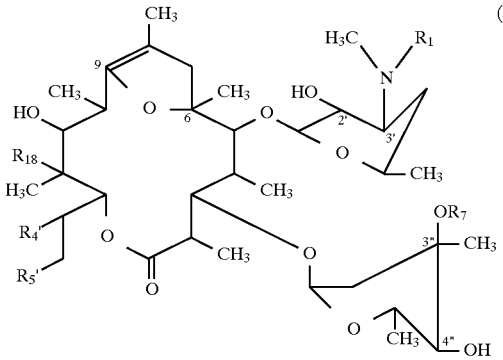
(18)

wherein $R_1$ represents hydrogen or a substituted or unsubstituted aliphatic hydrocarbon group, $R_{18}$ represents hydrogen or a hydroxyl group, $R_4'$ and $R_5'$ represent hydrogen or hydroxyl groups, $R_7$ represents hydrogen or a methyl group, wherein $R_7$ represents hydrogen when both of $R_4'$ and $R_5'$ are hydrogens, or the salt thereof, which comprises reacting a 6,9-hemiacetal-erythromycin compound represented by the formula (19):

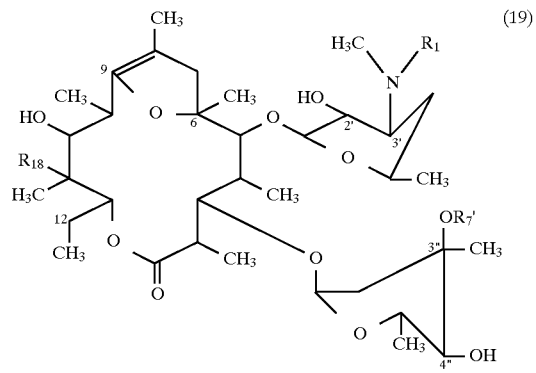
(19)

wherein $R_1$ and $R_{18}$ and have the same meaning as defined above, $R_7'$ represents hydrogen or a methyl group, or a salt thereof, with the oxidase derived from an actinomycete or a liver derived of a mammal.

23. The process according to claim 21, in which the actinomycete is an actinomycete belonging to Dactylosporangium, Saccharothrix or Amycolatopsis.

* * * * *